(12) United States Patent
McCormack et al.

(10) Patent No.: US 12,004,781 B2
(45) Date of Patent: Jun. 11, 2024

(54) LATERAL MASS FIXATION IMPLANT

(71) Applicant: Providence Medical Technology, Inc., Pleasanton, CA (US)

(72) Inventors: Bruce M. McCormack, San Francisco, CA (US); Edward Liou, Pleasanton, CA (US); Shigeru Tanaka, Half Moon Bay, CA (US); Christopher U. Phan, Dublin, CA (US); Jeffrey D. Smith, Clayton, CA (US); Todd Sheppard Saunders, Walnut Creek, CA (US); Krzysztof Siemionow, Chicago, IL (US)

(73) Assignee: Providence Medical Technology, Inc., Pleasanton, CA (US)

( * ) Notice: Subject to any disclaimer, the term of this patent is extended or adjusted under 35 U.S.C. 154(b) by 387 days.

(21) Appl. No.: 16/997,971

(22) Filed: Aug. 20, 2020

(65) Prior Publication Data

US 2020/0375633 A1 Dec. 3, 2020

Related U.S. Application Data

(63) Continuation of application No. 14/723,243, filed on May 27, 2015, now abandoned.

(Continued)

(51) Int. Cl.
*A61B 17/70* (2006.01)
*A61B 17/56* (2006.01)

(52) U.S. Cl.
CPC ...... *A61B 17/7064* (2013.01); *A61B 17/7002* (2013.01); *A61B 2017/564* (2013.01); *A61B 17/7035* (2013.01)

(58) Field of Classification Search
CPC ............ A61B 17/7064; A61B 17/7062; A61F 2/4405
See application file for complete search history.

(56) References Cited

U.S. PATENT DOCUMENTS

| 1,934,962 A | 11/1933 | Barry |
| 2,708,376 A | 5/1955 | Booth |

(Continued)

FOREIGN PATENT DOCUMENTS

| DE | G9304368.6 U1 | 5/2003 |
| FR | 2722980 A1 | 2/1996 |

(Continued)

OTHER PUBLICATIONS

US 7,063,700 B2, 06/2006, Michelson (withdrawn)
(Continued)

*Primary Examiner* — Julianna N Harvey
(74) *Attorney, Agent, or Firm* — Dorsey & Whitney LLP

(57) ABSTRACT

The various embodiments described herein provide lateral mass and facet fixation implants, which may be inserted and applied via a posterior approach, using minimally invasive or less invasive techniques. The embodiments described below generally include an intrafacet implant (or "facet implant") and a lateral mass fixation member attached to or attachable to the facet implant. The lateral mass fixation member can include one or more tabs extending from a middle portion and configured to secure the lateral mass fixation member to lateral masses of adjacent vertebrae. The tabs may be flexible, semi-rigid, or rigid, and may be collapsible to facilitate insertion of the device. Methods for delivering the lateral mass and facet fixation implants are also described.

10 Claims, 20 Drawing Sheets

Related U.S. Application Data

(60) Provisional application No. 62/003,443, filed on May 27, 2014.

(56) References Cited

U.S. PATENT DOCUMENTS

| | | |
|---|---|---|
| 2,984,241 A | 5/1961 | Carlson |
| 3,486,505 A | 12/1969 | Morrison |
| 4,463,753 A | 8/1984 | Gustilo |
| 4,479,491 A | 10/1984 | Martin |
| 4,530,355 A | 7/1985 | Griggs |
| 4,604,995 A | 8/1986 | Stephens et al. |
| 4,736,738 A | 4/1988 | Lipovsek et al. |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,192,327 A | 3/1993 | Brantigan |
| 5,236,460 A | 8/1993 | Barber |
| 5,443,514 A | 8/1995 | Steffee |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich et al. |
| 5,554,191 A | 9/1996 | Lahille et al. |
| 5,571,109 A | 11/1996 | Bertagnoli |
| 5,571,191 A | 11/1996 | Fitz |
| 5,584,832 A | 12/1996 | Schlapfer et al. |
| 5,593,409 A | 1/1997 | Michelson |
| 5,632,747 A | 5/1997 | Scarborough et al. |
| 5,649,945 A | 7/1997 | Ray et al. |
| 5,653,763 A | 8/1997 | Errico et al. |
| 5,665,122 A | 9/1997 | Kambin |
| 5,674,295 A | 10/1997 | Ray et al. |
| 5,702,443 A | 12/1997 | Braanemark |
| 5,720,748 A | 2/1998 | Kuslich et al. |
| 5,741,253 A | 4/1998 | Michelson |
| 5,772,661 A | 6/1998 | Michelson |
| 5,792,044 A | 8/1998 | Foley et al. |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz |
| 5,895,426 A | 4/1999 | Scarborough et al. |
| 5,899,908 A | 5/1999 | Kuslich et al. |
| 5,906,616 A | 5/1999 | Pavlov et al. |
| 5,928,238 A | 7/1999 | Scarborough et al. |
| 5,953,820 A | 9/1999 | Vasudeva |
| 5,961,522 A | 10/1999 | Mehdizadeh |
| 5,976,146 A | 11/1999 | Ogawa et al. |
| 6,008,433 A | 12/1999 | Stone |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,113,602 A | 9/2000 | Sand |
| 6,149,650 A | 11/2000 | Michelson |
| RE37,005 E | 12/2000 | Michelson et al. |
| 6,159,245 A | 12/2000 | Meriwether et al. |
| 6,174,311 B1 | 1/2001 | Branch et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,200,322 B1 | 3/2001 | Branch et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,245,108 B1 | 6/2001 | Biscup |
| 6,248,110 B1 | 6/2001 | Reiley et al. |
| 6,248,345 B1 | 6/2001 | Goldenheim et al. |
| D444,878 S | 7/2001 | Walter |
| D445,188 S | 7/2001 | Walter |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Boufburg |
| 6,315,795 B1 | 11/2001 | Scarborough et al. |
| 6,325,827 B1 | 12/2001 | Lin |
| 6,371,984 B1 | 4/2002 | Van Dyke et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,485,518 B1 | 11/2002 | Cornwall et al. |
| 6,500,206 B1 | 12/2002 | Bryan |
| 6,514,256 B2 | 2/2003 | Zucherman et al. |
| 6,524,312 B2 | 2/2003 | Landry et al. |
| 6,530,955 B2 | 3/2003 | Boyle et al. |
| 6,537,279 B1 | 3/2003 | Michelson |
| 6,540,747 B1 | 4/2003 | Marino |
| 6,558,390 B2 | 5/2003 | Cragg |
| 6,565,574 B2 | 5/2003 | Michelson |
| 6,565,605 B2 | 5/2003 | Fallin et al. |
| 6,569,186 B1 | 5/2003 | Winters et al. |
| 6,575,899 B1 | 6/2003 | Foley et al. |
| 6,575,919 B1 | 6/2003 | Reiley et al. |
| 6,575,979 B1 | 6/2003 | Cragg |
| 6,579,319 B2 | 6/2003 | Goble et al. |
| 6,582,432 B1 | 6/2003 | Michelson |
| 6,582,467 B1 | 6/2003 | Teitelbaum et al. |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |
| 6,719,773 B1 | 4/2004 | Boucher et al. |
| 6,719,794 B2 | 4/2004 | Gerber et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,814,738 B2 | 11/2004 | Naughton et al. |
| 6,823,871 B2 | 11/2004 | Schmieding |
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |

(56) References Cited

U.S. PATENT DOCUMENTS

| | | |
|---|---|---|
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,974,478 B2 | 12/2005 | Reiley et al. |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,029,479 B2 | 4/2006 | Tallarida et al. |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,090,698 B2 | 8/2006 | Fallin et al. |
| 7,096,972 B2 | 8/2006 | Orozco, Jr. |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,255,703 B2 | 8/2007 | Mujwid et al. |
| 7,261,739 B2 | 8/2007 | Ralph et al. |
| 7,264,622 B2 | 9/2007 | Michelson |
| 7,273,373 B2 | 9/2007 | Horiuchi |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,491,240 B1 | 2/2009 | Carver et al. |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,648,509 B2 | 1/2010 | Stark |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,708,766 B2 | 5/2010 | Anderson et al. |
| 7,722,619 B2 | 5/2010 | Michelson |
| D619,719 S | 7/2010 | Pannu |
| D620,113 S | 7/2010 | Courtney et al. |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Peterson |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,883,336 B2 | 2/2011 | Hansson |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,942,903 B2 | 5/2011 | Moskowitz et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |
| 8,062,299 B2 | 11/2011 | McGahan et al. |
| 8,062,303 B2 | 11/2011 | Berry et al. |
| 8,066,705 B2 | 11/2011 | Michelson |
| D650,481 S | 12/2011 | Gottlieb et al. |
| 8,092,475 B2 | 1/2012 | Cotter et al. |
| 8,097,034 B2 | 1/2012 | Michelson |
| 8,100,944 B2 | 1/2012 | Lauryssen et al. |
| D653,757 S | 2/2012 | Binder |
| 8,114,158 B2 | 2/2012 | Carl et al. |
| 8,118,838 B2 | 2/2012 | Winslow et al. |
| 8,128,660 B2 | 3/2012 | Mitchel et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,177,872 B2 | 5/2012 | Nelson et al. |
| 8,197,513 B2 | 6/2012 | Fisher et al. |
| 8,206,418 B2 | 6/2012 | Triplett et al. |
| 8,267,966 B2 | 9/2012 | McCormack et al. |
| 8,333,804 B1 | 12/2012 | Wensel |
| D674,900 S | 1/2013 | Janice et al. |
| 8,348,979 B2 | 1/2013 | McCormack |
| 8,361,152 B2 | 1/2013 | McCormack et al. |
| 8,366,748 B2 | 2/2013 | Kleiner |
| 8,382,767 B2 | 2/2013 | Wassinger et al. |
| D677,791 S | 3/2013 | Danacioglu et al. |
| 8,394,107 B2 | 3/2013 | Fanger et al. |
| 8,394,129 B2 | 3/2013 | Morgenstern et al. |
| D681,205 S | 4/2013 | Farris et al. |
| 8,425,558 B2 | 4/2013 | McCormack et al. |
| 8,439,922 B1 | 5/2013 | Arnold et al. |
| 8,512,347 B2 | 8/2013 | McCormack et al. |
| 8,518,090 B2 | 8/2013 | Huebner et al. |
| 8,523,908 B2 | 9/2013 | Malone |

(56) References Cited

U.S. PATENT DOCUMENTS

| | | |
|---|---|---|
| 8,529,609 B2 | 9/2013 | Helgerson et al. |
| 8,623,054 B2 | 1/2014 | McCormack et al. |
| 8,668,722 B2 | 3/2014 | Pavlov et al. |
| 8,753,345 B2 | 6/2014 | McCormack et al. |
| 8,753,347 B2 | 6/2014 | McCormack et al. |
| 8,764,755 B2 | 7/2014 | Michelson |
| 8,828,062 B2 | 9/2014 | McCormack et al. |
| 8,834,530 B2 | 9/2014 | McCormack |
| 8,845,727 B2 | 9/2014 | Gottlieb et al. |
| 8,870,882 B2 | 10/2014 | Kleiner |
| D723,690 S | 3/2015 | McCormack et al. |
| D723,691 S | 3/2015 | McCormack et al. |
| 8,998,905 B2 | 4/2015 | Marik et al. |
| 9,005,288 B2 | 4/2015 | McCormack et al. |
| 9,011,492 B2 | 4/2015 | McCormack et al. |
| 9,039,766 B1 | 5/2015 | Fonte |
| D732,667 S | 6/2015 | McCormack et al. |
| 9,186,193 B2 | 11/2015 | Kleiner et al. |
| D745,156 S | 12/2015 | McCormack et al. |
| 9,211,198 B2 | 12/2015 | Michelson |
| 9,220,608 B2 | 12/2015 | McKay |
| D750,249 S | 2/2016 | Grimberg, Jr. et al. |
| 9,271,765 B2 | 3/2016 | Blain |
| 9,333,086 B2 | 5/2016 | McCormack et al. |
| 9,339,263 B2 | 5/2016 | Fenn et al. |
| 9,358,127 B2 | 6/2016 | Duffield et al. |
| 9,381,049 B2 | 7/2016 | McCormack et al. |
| 9,427,264 B2 | 8/2016 | Kleiner et al. |
| 9,504,583 B2 | 11/2016 | Blain |
| 9,622,791 B2 | 4/2017 | McCormack et al. |
| 9,622,873 B2 | 4/2017 | McCormack et al. |
| 9,622,874 B2 | 4/2017 | McCormack et al. |
| 9,629,665 B2 | 4/2017 | McCormack et al. |
| 9,707,650 B2 | 7/2017 | Tiefenbock |
| 9,717,403 B2 | 8/2017 | Kleiner et al. |
| 9,937,053 B2 | 4/2018 | Melkent et al. |
| 10,039,649 B2 | 8/2018 | McCormack et al. |
| 10,149,673 B2 | 12/2018 | McCormack et al. |
| 10,172,721 B2 | 1/2019 | McCormack et al. |
| D841,165 S | 2/2019 | McCormack et al. |
| D841,167 S | 2/2019 | Ricca et al. |
| 10,201,375 B2 | 2/2019 | McCormack et al. |
| 10,206,787 B2 | 2/2019 | Voellmicke |
| 10,219,910 B2 | 3/2019 | McCormack et al. |
| 10,226,285 B2 | 3/2019 | McCormack et al. |
| 10,238,501 B2 | 3/2019 | McCormack et al. |
| 10,327,913 B2 | 6/2019 | Palmatier et al. |
| 10,456,175 B2 | 10/2019 | McCormack et al. |
| 10,568,666 B2 | 2/2020 | McCormack et al. |
| 10,588,672 B2 | 3/2020 | McCormack et al. |
| D884,895 S | 5/2020 | McCormack et al. |
| D887,552 S | 6/2020 | Tanaka et al. |
| 10,682,243 B2 | 6/2020 | Phan et al. |
| D911,525 S | 2/2021 | Tanaka et al. |
| 10,907,417 B2 | 2/2021 | Brady |
| RE48,501 E | 4/2021 | McCormack et al. |
| 11,058,466 B2 | 7/2021 | McCormack et al. |
| 11,272,964 B2 | 3/2022 | McCormack et al. |
| 11,285,010 B2 | 3/2022 | McCormack |
| 11,648,128 B2 | 5/2023 | Tanaka et al. |
| 2001/0004710 A1 | 6/2001 | Felt et al. |
| 2001/0007074 A1 | 7/2001 | Strobel et al. |
| 2001/0047208 A1 | 11/2001 | Michelson |
| 2001/0053914 A1 | 12/2001 | Landry et al. |
| 2002/0026195 A1 | 2/2002 | Layne et al. |
| 2002/0068941 A1 | 6/2002 | Hanson et al. |
| 2002/0077641 A1 | 6/2002 | Michelson |
| 2002/0107519 A1 | 8/2002 | Dixon et al. |
| 2002/0143343 A1 | 10/2002 | Castro |
| 2002/0147496 A1 | 10/2002 | Belef et al. |
| 2002/0165612 A1 | 11/2002 | Gerber et al. |
| 2002/0169471 A1 | 11/2002 | Ferdinand |
| 2002/0177866 A1 | 11/2002 | Weikel et al. |
| 2003/0023312 A1 | 1/2003 | Thalgott |
| 2003/0028251 A1 | 2/2003 | Mathews |
| 2003/0032962 A1 | 2/2003 | McGahan et al. |
| 2003/0033017 A1 | 2/2003 | Lotz et al. |
| 2003/0040801 A1 | 2/2003 | Ralph et al. |
| 2003/0060887 A1 | 3/2003 | Ek |
| 2003/0077134 A1 | 4/2003 | Moser et al. |
| 2003/0083668 A1 | 5/2003 | Rogers et al. |
| 2003/0083688 A1 | 5/2003 | Simonson |
| 2003/0105526 A1 | 6/2003 | Bryant et al. |
| 2003/0109928 A1 | 6/2003 | Pasquet et al. |
| 2003/0120276 A1 | 6/2003 | Tallarida et al. |
| 2003/0139816 A1 | 7/2003 | Michelson |
| 2003/0144737 A1 | 7/2003 | Sherman |
| 2003/0149438 A1 | 8/2003 | Nichols et al. |
| 2003/0158553 A1 | 8/2003 | Michelson |
| 2003/0225416 A1 | 12/2003 | Bonvallet et al. |
| 2004/0010259 A1 | 1/2004 | Keller et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochshculer et al. |
| 2004/0225292 A1 | 11/2004 | Sasso et al. |
| 2004/0254575 A1 | 12/2004 | Obenchain et al. |
| 2005/0010294 A1 | 1/2005 | Michelson |
| 2005/0015097 A1 | 1/2005 | Mujwid et al. |
| 2005/0015149 A1 | 1/2005 | Michelson |
| 2005/0021042 A1 | 1/2005 | Marnay et al. |
| 2005/0027358 A1 | 2/2005 | Suddaby |
| 2005/0033432 A1 | 2/2005 | Gordon et al. |
| 2005/0038511 A1 | 2/2005 | Martz et al. |
| 2005/0049623 A1 | 3/2005 | Moore et al. |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065608 A1 | 3/2005 | Michelson |
| 2005/0065609 A1 | 3/2005 | Wardlaw |
| 2005/0080422 A1 | 4/2005 | Otte et al. |
| 2005/0085912 A1 | 4/2005 | Arnin et al. |
| 2005/0090829 A1 | 4/2005 | Martz et al. |
| 2005/0090901 A1 | 4/2005 | Studer |
| 2005/0113842 A1 | 5/2005 | Bertagnoli et al. |
| 2005/0119680 A1 | 6/2005 | Dykes |
| 2005/0124993 A1 | 6/2005 | Chappuis |
| 2005/0143818 A1 | 6/2005 | Yuan et al. |
| 2005/0149192 A1 | 7/2005 | Zucherman et al. |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0209698 A1 | 9/2005 | Gordon et al. |
| 2005/0216018 A1 | 9/2005 | Sennett |
| 2005/0234455 A1 | 10/2005 | Binder et al. |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0251260 A1 | 11/2005 | Gerber et al. |
| 2005/0267480 A1 | 12/2005 | Suddaby |
| 2006/0004367 A1 | 1/2006 | Alamin et al. |
| 2006/0004448 A1 | 1/2006 | Casey |
| 2006/0015184 A1 | 1/2006 | Winterbottom et al. |
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058790 A1 | 3/2006 | Carl et al. |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry |
| 2006/0085074 A1 | 4/2006 | Raiszadeh |
| 2006/0095028 A1 | 5/2006 | Bleich |
| 2006/0095036 A1 | 5/2006 | Hammerslag |

(56) References Cited

U.S. PATENT DOCUMENTS

| | | |
|---|---|---|
| 2006/0111779 A1 | 5/2006 | Peterson |
| 2006/0111780 A1 | 5/2006 | Petersen |
| 2006/0111781 A1 | 5/2006 | Petersen |
| 2006/0142762 A1 | 6/2006 | Michelson |
| 2006/0149279 A1 | 7/2006 | Mathews |
| 2006/0149289 A1 | 7/2006 | Winslow et al. |
| 2006/0184172 A1 | 8/2006 | Michelson |
| 2006/0189991 A1 | 8/2006 | Bickley |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0229627 A1 | 10/2006 | Hunt et al. |
| 2006/0235306 A1 | 10/2006 | Cotter et al. |
| 2006/0235391 A1 | 10/2006 | Sutterlin |
| 2006/0235414 A1 | 10/2006 | Lim et al. |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1 | 3/2007 | Khosrowshahi |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0162138 A1 | 7/2007 | Heinz |
| 2007/0179617 A1 | 8/2007 | Brown et al. |
| 2007/0179619 A1 | 8/2007 | Grob et al. |
| 2007/0191861 A1 | 8/2007 | Allard et al. |
| 2007/0225721 A1 | 9/2007 | Thelen et al. |
| 2007/0225812 A1 | 9/2007 | Gill |
| 2007/0244483 A9 | 10/2007 | Winslow et al. |
| 2007/0250167 A1 | 10/2007 | Bray et al. |
| 2007/0276491 A1 | 11/2007 | Ahrens |
| 2007/0282441 A1 | 12/2007 | Stream et al. |
| 2007/0288014 A1 | 12/2007 | Shadduck et al. |
| 2007/0293949 A1 | 12/2007 | Salerni et al. |
| 2007/0299451 A1 | 12/2007 | Tulkis |
| 2008/0015581 A1 | 1/2008 | Eckman |
| 2008/0021457 A1 | 1/2008 | Anderson et al. |
| 2008/0021464 A1 | 1/2008 | Morin et al. |
| 2008/0058954 A1 | 3/2008 | Trieu |
| 2008/0065219 A1 | 3/2008 | Dye |
| 2008/0071375 A1 | 3/2008 | Carver et al. |
| 2008/0077245 A1 | 3/2008 | Lee |
| 2008/0091269 A1 | 4/2008 | Zipnick et al. |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0154377 A1 | 6/2008 | Voellmicke |
| 2008/0161810 A1 | 7/2008 | Melkent |
| 2008/0161929 A1 | 7/2008 | McCormack et al. |
| 2008/0167657 A1 | 7/2008 | Greenhaigh |
| 2008/0177311 A1 | 7/2008 | Winslow et al. |
| 2008/0183209 A1 | 7/2008 | Robinson et al. |
| 2008/0195206 A1 | 8/2008 | Chee et al. |
| 2008/0208341 A1 | 8/2008 | McCormack et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0249571 A1 | 10/2008 | Sasso et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0275455 A1 | 11/2008 | Berry et al. |
| 2008/0287955 A1 | 11/2008 | Michelson |
| 2008/0300685 A1 | 12/2008 | Carls et al. |
| 2008/0306537 A1 | 12/2008 | Culbert |
| 2008/0312744 A1 | 12/2008 | Vresilovic et al. |
| 2009/0036927 A1 | 2/2009 | Vestgaarden |
| 2009/0131986 A1 | 5/2009 | Lee et al. |
| 2009/0138053 A1 | 5/2009 | Assell et al. |
| 2009/0177205 A1 | 7/2009 | McCormack et al. |
| 2009/0177215 A1 | 7/2009 | Stack et al. |
| 2009/0177237 A1 | 7/2009 | Zucherman et al. |
| 2009/0182429 A1 | 7/2009 | Humphreys et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1* | 10/2009 | Suddaby ............ A61B 17/7064 606/301 |
| 2009/0275994 A1 | 11/2009 | Phan et al. |
| 2009/0297603 A1 | 12/2009 | Joshi |
| 2009/0306671 A1* | 12/2009 | McCormack ...... A61B 17/8004 606/90 |
| 2009/0312763 A1 | 12/2009 | McCormack et al. |
| 2010/0036418 A1 | 2/2010 | Siemionow et al. |
| 2010/0069912 A1 | 3/2010 | McCormack et al. |
| 2010/0082065 A1 | 4/2010 | Butler et al. |
| 2010/0086185 A1 | 4/2010 | Weiss |
| 2010/0093829 A1 | 4/2010 | Gorman |
| 2010/0111829 A1 | 5/2010 | Drapeau et al. |
| 2010/0114318 A1 | 5/2010 | Gittings et al. |
| 2010/0145391 A1 | 6/2010 | Kleiner |
| 2010/0145459 A1 | 6/2010 | Mcdonough et al. |
| 2010/0161057 A1 | 6/2010 | Berry et al. |
| 2010/0191241 A1 | 7/2010 | McCormack et al. |
| 2010/0211104 A1 | 8/2010 | Moumene et al. |
| 2010/0286783 A1 | 11/2010 | Lechmann et al. |
| 2011/0004247 A1 | 1/2011 | Lechmann et al. |
| 2011/0022089 A1 | 1/2011 | Assell et al. |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0098756 A1 | 4/2011 | Brannon |
| 2011/0144755 A1 | 6/2011 | Baynham et al. |
| 2011/0184470 A1 | 7/2011 | Gorek et al. |
| 2011/0190821 A1* | 8/2011 | Chin .................... A61B 17/864 606/264 |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |
| 2012/0029545 A1 | 2/2012 | Nelson et al. |
| 2012/0065613 A1 | 3/2012 | Pepper et al. |
| 2012/0130496 A1 | 5/2012 | Duffield et al. |
| 2012/0143334 A1 | 6/2012 | Boyce et al. |
| 2012/0179259 A1 | 7/2012 | Mcdonough et al. |
| 2012/0215259 A1 | 8/2012 | Cannestra |
| 2012/0245637 A1 | 9/2012 | Kraus et al. |
| 2012/0245689 A1 | 9/2012 | Gimbel et al. |
| 2012/0265250 A1 | 10/2012 | Ali |
| 2012/0277801 A1 | 11/2012 | Marik et al. |
| 2012/0283776 A1 | 11/2012 | Mishra |
| 2012/0296431 A1 | 11/2012 | Kim et al. |
| 2012/0323242 A1 | 12/2012 | Tsuang et al. |

(56) References Cited

U.S. PATENT DOCUMENTS

| | | |
|---|---|---|
| 2013/0006364 A1 | 1/2013 | McCormack et al. |
| 2013/0012994 A1 | 1/2013 | McCormack et al. |
| 2013/0013070 A1 | 1/2013 | McCormack et al. |
| 2013/0018474 A1 | 1/2013 | McCormack et al. |
| 2013/0023889 A1 | 1/2013 | Blain et al. |
| 2013/0023995 A1 | 1/2013 | McCormack et al. |
| 2013/0023996 A1 | 1/2013 | McCormack et al. |
| 2013/0030440 A1 | 1/2013 | McCormack et al. |
| 2013/0030532 A1 | 1/2013 | McCormack et al. |
| 2013/0110168 A1 | 5/2013 | McCormack et al. |
| 2013/0110243 A1 | 5/2013 | Patterson et al. |
| 2013/0123922 A1 | 5/2013 | McCormack et al. |
| 2013/0123923 A1 | 5/2013 | Pavlov et al. |
| 2013/0144389 A1 | 6/2013 | Bonutti |
| 2013/0226239 A1 | 8/2013 | Altarac et al. |
| 2013/0238095 A1 | 9/2013 | Pavento et al. |
| 2013/0253649 A1 | 9/2013 | Davis |
| 2013/0274763 A1 | 10/2013 | Drapeau et al. |
| 2013/0310839 A1 | 11/2013 | McCormack et al. |
| 2013/0310878 A1 | 11/2013 | McCormack et al. |
| 2013/0310943 A1 | 11/2013 | McCormack et al. |
| 2013/0317548 A1 | 11/2013 | Malone |
| 2013/0338720 A1 | 12/2013 | Kleiner |
| 2014/0012318 A1 | 1/2014 | Goel |
| 2014/0025113 A1 | 1/2014 | McCormack et al. |
| 2014/0066758 A1 | 3/2014 | Marik et al. |
| 2014/0100657 A1 | 4/2014 | McCormack et al. |
| 2014/0114415 A1 | 4/2014 | Tyber |
| 2014/0135930 A1 | 5/2014 | Georges |
| 2014/0172103 A1 | 6/2014 | O'neil et al. |
| 2014/0228959 A1 | 8/2014 | Niemiec et al. |
| 2014/0296916 A1 | 10/2014 | Mccormack et al. |
| 2014/0379087 A1 | 12/2014 | McCormack |
| 2015/0025635 A1 | 1/2015 | Laubert |
| 2015/0088200 A1 | 3/2015 | Lins |
| 2015/0100129 A1 | 4/2015 | Waugh et al. |
| 2015/0201977 A1 | 7/2015 | Mccormack et al. |
| 2015/0230834 A1 | 8/2015 | Cannestra |
| 2015/0297357 A1 | 10/2015 | McCormack et al. |
| 2015/0328005 A1 | 11/2015 | Padovani et al. |
| 2015/0328010 A1 | 11/2015 | Martynova et al. |
| 2015/0342617 A1 | 12/2015 | Kunz et al. |
| 2015/0342648 A1 | 12/2015 | Mccormack et al. |
| 2015/0342649 A1 | 12/2015 | Mccormack et al. |
| 2016/0008040 A1 | 1/2016 | Mccormack et al. |
| 2016/0242754 A1 | 8/2016 | Mccormack et al. |
| 2016/0250035 A1 | 9/2016 | De Villiers et al. |
| 2016/0317316 A1 | 11/2016 | Mccormack et al. |
| 2016/0331553 A1 | 11/2016 | Liou et al. |
| 2017/0027713 A1 | 2/2017 | Kleiner |
| 2017/0135733 A1 | 5/2017 | Donner et al. |
| 2017/0189199 A1 | 7/2017 | Maier et al. |
| 2017/0216044 A1 | 8/2017 | McCormack et al. |
| 2017/0281360 A1 | 10/2017 | Seifert |
| 2017/0348027 A1 | 12/2017 | McCormack et al. |
| 2017/0354444 A1 | 12/2017 | McCormack et al. |
| 2017/0360571 A1 | 12/2017 | Mesiwala |
| 2018/0161077 A1 | 6/2018 | McCormack et al. |
| 2018/0168772 A1 | 6/2018 | Abboud et al. |
| 2018/0303623 A1 | 10/2018 | Shoshtaev |
| 2018/0303631 A1 | 10/2018 | Phan et al. |
| 2019/0083271 A1 | 3/2019 | Donner et al. |
| 2019/0209151 A1 | 7/2019 | McCormack et al. |
| 2019/0239932 A1 | 8/2019 | McCormack et al. |
| 2019/0240041 A1 | 8/2019 | McCormack et al. |
| 2019/0247099 A1 | 8/2019 | McCormack et al. |
| 2019/0307571 A1 | 10/2019 | McCormack et al. |
| 2019/0307572 A1 | 10/2019 | McCormack et al. |
| 2019/0350626 A1 | 11/2019 | McCormack et al. |
| 2020/0085475 A1 | 3/2020 | McCormack et al. |
| 2020/0155205 A1 | 5/2020 | Tanaka et al. |
| 2020/0289285 A1 | 9/2020 | Siemionow et al. |
| 2020/0405502 A1 | 12/2020 | Gephart et al. |
| 2021/0022881 A1 | 1/2021 | McCormack et al. |
| 2021/0059833 A1 | 3/2021 | Tanaka et al. |
| 2021/0378720 A1 | 12/2021 | McCormack et al. |
| 2021/0386434 A1 | 12/2021 | Tanaka et al. |
| 2022/0031297 A1 | 2/2022 | McCormack et al. |
| 2022/0151663 A1 | 5/2022 | McCormack et al. |
| 2022/0211513 A1 | 7/2022 | McCormack et al. |
| 2022/0287742 A1 | 9/2022 | McCormack et al. |
| 2022/0313448 A1 | 10/2022 | McCormack |
| 2022/0323117 A1 | 10/2022 | Phan et al. |
| 2023/0139017 A1 | 5/2023 | McCormack et al. |
| 2023/0149179 A1 | 5/2023 | McCormack et al. |
| 2023/0181327 A1 | 6/2023 | Tanaka et al. |

FOREIGN PATENT DOCUMENTS

| | | |
|---|---|---|
| JP | H11508781 A | 8/1999 |
| JP | 2004523288 A | 8/2004 |
| JP | 2008509735 A | 4/2008 |
| JP | 2008522787 A | 7/2008 |
| JP | 2012501234 A | 1/2012 |
| JP | 2014516268 A | 7/2014 |
| WO | 9641582 A1 | 12/1996 |
| WO | 99/49818 A1 | 10/1999 |
| WO | 00/035388 A1 | 6/2000 |
| WO | 00/53126 A1 | 9/2000 |
| WO | 01/01895 A1 | 1/2001 |
| WO | 02/34120 A2 | 5/2002 |
| WO | 02/038062 A2 | 5/2002 |
| WO | 02/076335 A2 | 10/2002 |
| WO | 2005032358 A2 | 4/2005 |
| WO | 2006058221 A2 | 6/2006 |
| WO | 2006130791 A2 | 12/2006 |
| WO | 2007120903 A2 | 10/2007 |
| WO | 2008083349 A1 | 7/2008 |
| WO | 2008127978 A2 | 10/2008 |
| WO | 2008153732 A1 | 12/2008 |
| WO | 2009089367 A2 | 7/2009 |
| WO | 2009148619 A2 | 12/2009 |
| WO | 2010030994 A2 | 3/2010 |
| WO | 2010074714 A2 | 7/2010 |
| WO | 2010107692 A1 | 9/2010 |
| WO | 2011050140 A1 | 4/2011 |
| WO | 2013043584 A2 | 3/2013 |
| WO | 2014188280 A2 | 11/2014 |
| WO | 2016049784 A1 | 4/2016 |

OTHER PUBLICATIONS

Spinal News International, "FDA clears Renovis Surgical 3D-printed titanium standalone cervical cage", first available Apr. 11, 2016. https://spinalnewsinternational.com/fda-clears-renovis-surgical-3d-printed-titanium-standalone-cervical-cage/.

Research Gate, "DTRAX Posterior Cervical Cage", first available Jul. 2016. (hllps://www.researchgate.net/figure/ DTRAX-Posterior-Cervical-Cage-Note-The-cervical-cages-are-manufactured-from-implant_fig3_305314436).

Providence Medical Technology, "Cavux Cervical Cages", first available Oct. 5, 2016. (hllps://web.archive.org/web/20161005063842/https:/providencemt.com/cavux-cervical-cages/).

Providence Medical Technology, "Posterior Cervical Stabilization System (PCSS)", first available Jun. 21, 2020. (hllps://web.archive.org/web/20200621181620/hllps:/providencemt.com/pcss/).

Atul Goel, Facetal distraction as treatment for single- and multilevel cervical spondylotic radiculopathy and myelopathy: a preliminary report, J Neurosurg Spine, Jun. 2011, pp. 689-696.

Press Release, Interventional Spine, Inc., Interventional Spine, Inc. Introduces the PERPOS Fusion Facet Prep Kit, Oct. 14, 2008, 1 Page.

Press Release, minSURG Corp., Orthopedic Development Corporation's TruFUSE Procedure Tops 1,750 Patients in First Year, Sep. 24, 2007, 1 Page.

(56) References Cited

OTHER PUBLICATIONS

Press Release, Interventional Spine, Inc., FDA Grants Conditional Approval to Interventional Spine's PercuDyn System IDE Application, Jul. 1, 2008, 1 Page.
Stein, et al., "Percutaneous Facet Joint Fusion: Preliminary Experience," Journal of Vascular and Interventional Radiology, Jan.-Feb. 1993, pp. 69-74, vol. 4, No. 1.

\* cited by examiner

LATERAL MASS FIXATION IMPLANT

CROSS-REFERENCE TO RELATED APPLICATIONS

This application is a continuation of U.S. patent application Ser. No. 14/723,243, filed May 27, 2015 entitled "Lateral Mass Fixation Implant," which claims priority to U.S. Provisional Patent Application No. 62/003,443, entitled "Lateral Mass Fixation Implant," filed on May 27, 2014, the entirety of each of which is hereby incorporated by reference.

BACKGROUND

Posterior cervical fusion with lateral mass fixation is the most rigid cervical instrumentation. It requires extensive dissection of muscles and ligaments off the posterior spine, so that the surgeon can have direct visualization to safely perform the procedure. This dissection causes acute and chronic soft tissue pain syndrome. Acutely, patients are typically hospitalized for three to four days for pain control that requires IV narcotics. This is compared to one-day hospitalization for anterior approaches that do not require any muscle or soft tissue dissection. Long-term patients with posterior approaches frequently have persistent pain due to the extensive nature of the dissection. Sometimes, after posterior-access cervical fusion surgery, soft tissues may not return to anatomic position and may be permanently deformed. Persistent pain after posterior surgical approaches is referred to as post-laminectomy syndrome. (FIG. 1 is a lateral view of the C5 and C6 cervical vertebrae, illustrating the anatomy.)

Therefore, since it is considered less traumatic to the patient compared to posterior approaches, anterior cervical spinal fusion surgery has generally been preferred over posterior fusion surgery. At the same time, posterior approaches to the cervical spine do have some advantages over anterior approaches.

Lateral mass or pedicle screw fixation provides more rigid fixation of the cervical spine than anterior plates, interbody devices and interspinous wiring. It is best for traumatic instability, but it has also been used for degenerative conditions. Despite being the best fixation, lateral mass fixation is often avoided, because of the morbidity of the soft tissue dissection, as noted above. (FIGS. 2A and 2B are posterior and lateral views, respectively, of a cervical spine with posterior fixation devices applied thereto.)

Starting a drill hole or inserting a screw into a lateral mass of a vertebra cannot currently be accomplished using a percutaneous approach. This is because soft tissue gets caught up in the drill, and the drill can skid off the bone and go out of control. Awls and firm pressure placed on bone with screws without direct visualization is dangerous in the posterior cervical spine, unless the surgeon has removed soft tissue and has direct visualization.

Therefore, it would be advantageous to have improved devices, systems and methods for performing cervical spinal fusion procedures via posterior access approaches. Ideally, these devices, systems and methods would allow for minimally invasive or less invasive access and fixation, as well as helping ensure proper placement of the fixation devices. At least some of these objectives will be met by the embodiments described herein.

BRIEF SUMMARY

The various embodiments described herein provide lateral mass and facet fixation implants, which may be inserted and applied via a posterior approach, using minimally invasive or less invasive techniques. The embodiments described below generally include an intrafacet implant (or "facet implant") and a lateral mass fixation member attached to or attachable to the facet implant. The lateral mass fixation member can include one or more tabs extending from a middle portion and configured to secure the lateral mass fixation member to lateral masses of adjacent vertebrae. The tabs may be flexible, semi-rigid, or rigid, and may be collapsible to facilitate insertion of the member.

In one aspect, a spinal implant system is disclosed. The spinal implant system includes a facet implant member for positioning in a facet joint and a lateral mass fixation member attached to or attachable to the facet implant member. The facet implant member and the lateral mass fixation member may be two separate devices or components that are attachable in situ or they may be a single device or of a single piece or monolithic construction. In some embodiments, the facet implant member includes a peg and the lateral mass fixation member includes a hole formed therethrough for receiving the peg. The peg may have one of a round shape, a square shape, and a polygonal shape.

In some aspects, the lateral mass fixation member includes a plate, the plate including a middle portion, an opening in the middle portion configured to allow passage of a screw to connect the plate with the facet implant member, and two tabs extending from opposite sides of the middle portion to contact lateral masses of adjacent vertebrae. The tabs may include one or more surface features, such as spikes, extending from the tabs for securing the tabs to the lateral masses of adjacent vertebrae. The tabs may include one or more holes formed therethrough to receive one or more fixation devices configured to secure the tabs to the lateral masses of adjacent vertebrae. The tabs may extend from the sides of the middle portion via hinges and the tabs are rotatable about the hinges relative to the middle portion. The lateral mass fixation member may include two tabs that extend from the facet implant member to contact lateral masses of adjacent vertebrae. The tabs may be moveable from a collapsed configuration for delivery of the system into a patient to an expanded configuration for attachment to lateral masses of adjacent vertebrae.

In some aspects, the system may further include a guide member for guiding at least one of the facet implant member or the lateral mass fixation member to a spine for attachment thereto.

In some aspects, the lateral mass fixation member includes a first face configured to attach to the facet implant member, and a second face coupled to and forming an angle with the first face, wherein the second face is configured to secure the lateral mass fixation member to lateral masses of adjacent vertebrae.

In some aspects, the lateral mass fixation member includes an anchor including an attachment device for attaching to the facet implant and a rod receiving member. The fixation member further includes a rod having a length sufficient to contact lateral masses of adjacent vertebrae.

A method for implanting a spinal fixation implant is disclosed. The method includes inserting a facet implant member in a facet joint and attaching a lateral mass fixation member to the facet implant member. In some embodiments, attaching the lateral mass fixation member includes screwing the lateral mass fixation member to the facet implant member. The method may further include attaching a guide rod to the facet implant member, positioning the lateral fixation member adjacent to the facet implant via the guide rod, and removing the guide rod. In some embodiments, inserting the facet implant includes delivering the facet implant via a guide tube.

A method for implanting a spinal fixation implant is disclosed. In one aspect, the method includes inserting a facet implant member of a fixation system in a facet joint, and expanding a lateral mass fixation member of the fixation system to contact lateral masses of adjacent vertebrae. In some aspects, the method further includes attaching the lateral mass fixation member to the lateral masses using at least one screw.

These and other aspects and embodiments will be described in further detail below, in reference to the attached drawing figures.

DETAILED DESCRIPTION

The various embodiments described herein include a system for providing lateral mass fixation in the cervical spine, using posterior access, less invasive or minimally invasive, insertion methods. Generally, each system includes a facet component and a lateral mass fixation component. In some embodiments, the facet component and the lateral mass fixation component are separate devices until they are attached in situ within the patient. In other embodiments, the facet and lateral mass fixation components may be combined into one device. Some embodiments may include simply a facet implant by itself, which may be attached to one or more lateral mass fixation devices or members. Similarly, a lateral mass fixation device or member may be provided by itself, and may be compatible with one or more facet implant devices. The embodiments described herein also include methods for inserting, implanting and attaching the facet components and lateral fixation components described herein.

Lateral mass instrumentation may include a screw, staple or post in the lateral mass. Additional instrumentation such as a rod or plate may be used as a tension band to connect the rostral and caudal facet. This additional instrumentation may serve to limit flexion and extension as well as lateral bending. The facet implant connects with and/or helps guide the fixation member (or tension band) into place. The tension band device (e.g., plate, screw, rod or other material that bridges the rostral and caudal lateral mass) may be modular. It can be used to cross one or multiple motion segments. It may be put in before or after the facet implant. The combination of the facet implant and the lateral mass fixation member will provide superior fixation and stability of the joint in both the flexion and extension directions.

The surgeon may insert the facet implant though a minimal access incision, using an insertion system such as, but not limited to, the DTRAX® Spinal System, from Providence Medical Technology, Inc. (www.providencemt.com). A facet implant that may be used in the embodiments described herein includes the DTRAX® Cervical Cage, from Providence Medical Technology, Inc. (www.providencemt.com). The fixed point deep in the spine that is provided by the facet implant can be used to instrument the posterior cervical spine beyond the facet, from a percutaneous approach, without direct visualization. This avoids stripping all the soft tissue off the spine. A fixed point deep in the patient's spine prevents instruments from slipping off the spine and allows for location, alignment, and anchoring for fixation instrumentation. Also, the cervical facet has a fixed anatomic relationship to lateral mass bone consistent in all patients. Fixation instrumentation can be positioned off the facet implant to reliable landmarks on the lateral mass without direct visualization.

Figure 1:
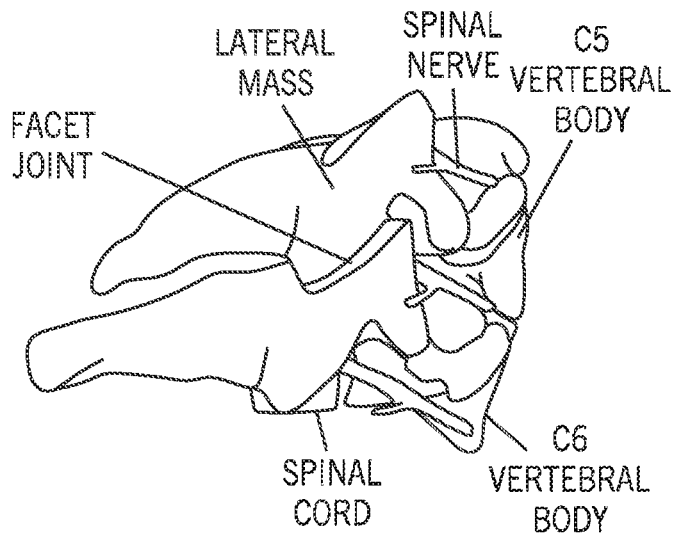
FIG. 1 is a lateral view of the C5 and C6 cervical vertebrae, illustrating the anatomy.
Figure 2A:
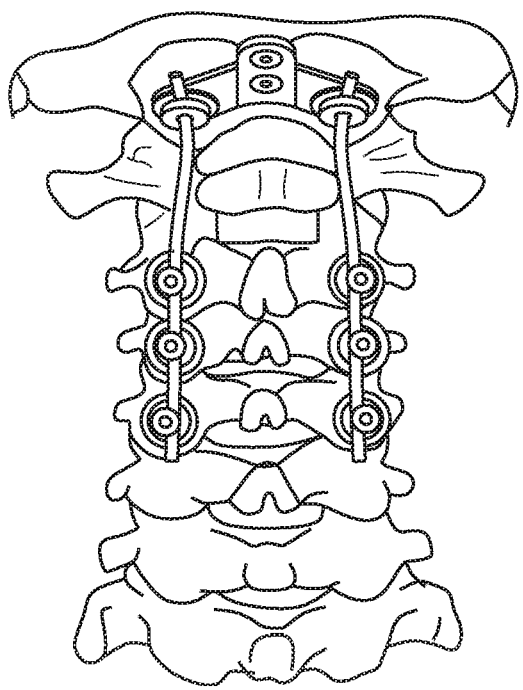
FIGS. 2A and 2B are posterior and lateral views, respectively, of a cervical spine with prior art posterior fixation devices applied thereto.
Figure 2B:
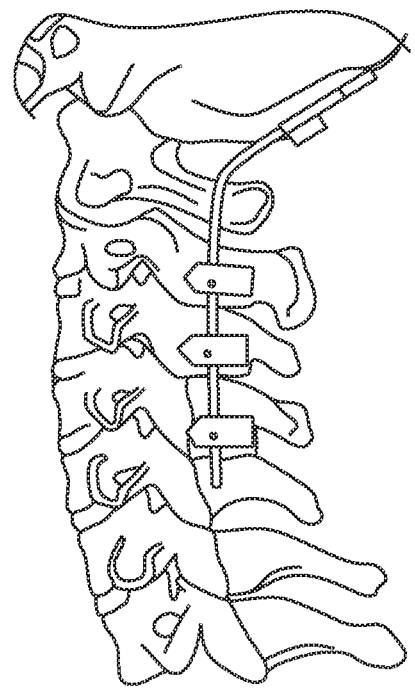
Figure 3A:
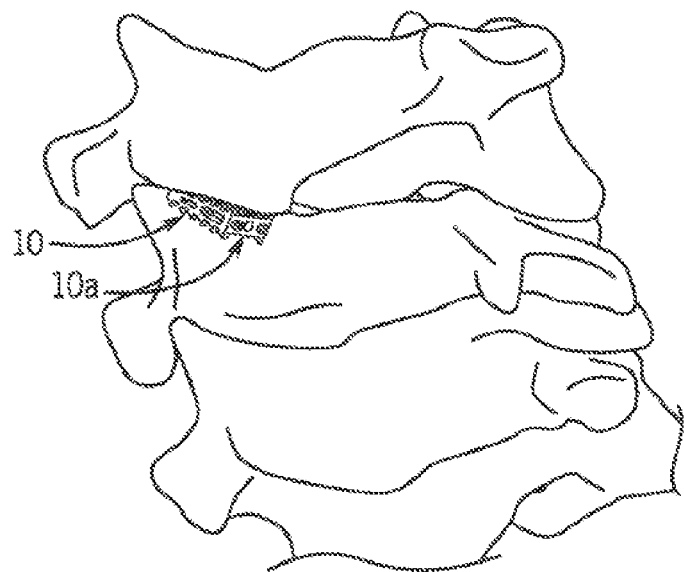
FIGS. 3A-3D are perspective (3A-3C) and lateral cross-sectional (3D) views of a portion of a cervical spine, illustrating a facet implant and a method for attaching a lateral mass fixation member thereto, according to one embodiment.
Figure 3B:
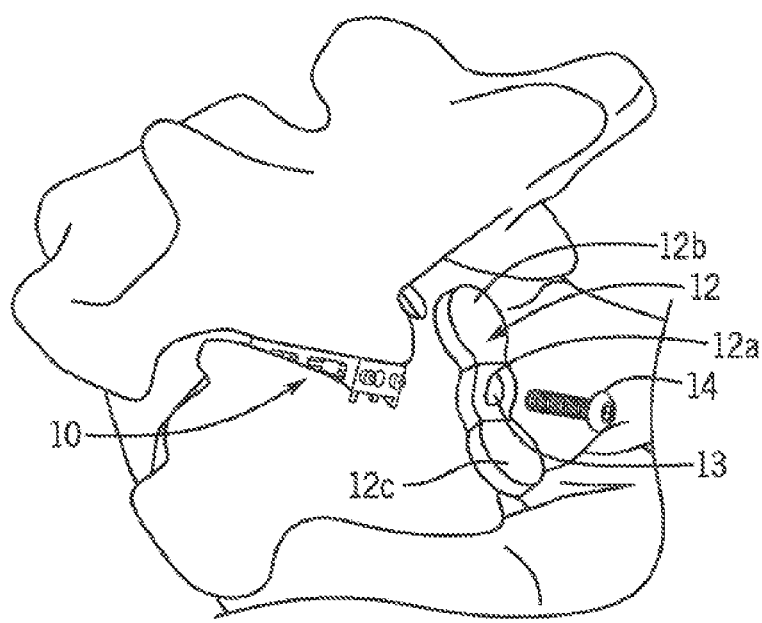
Figure 3C:
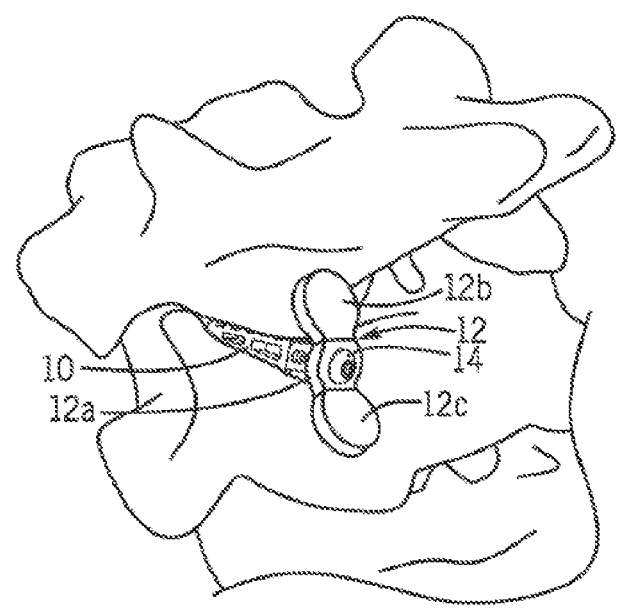
Figure 3D:
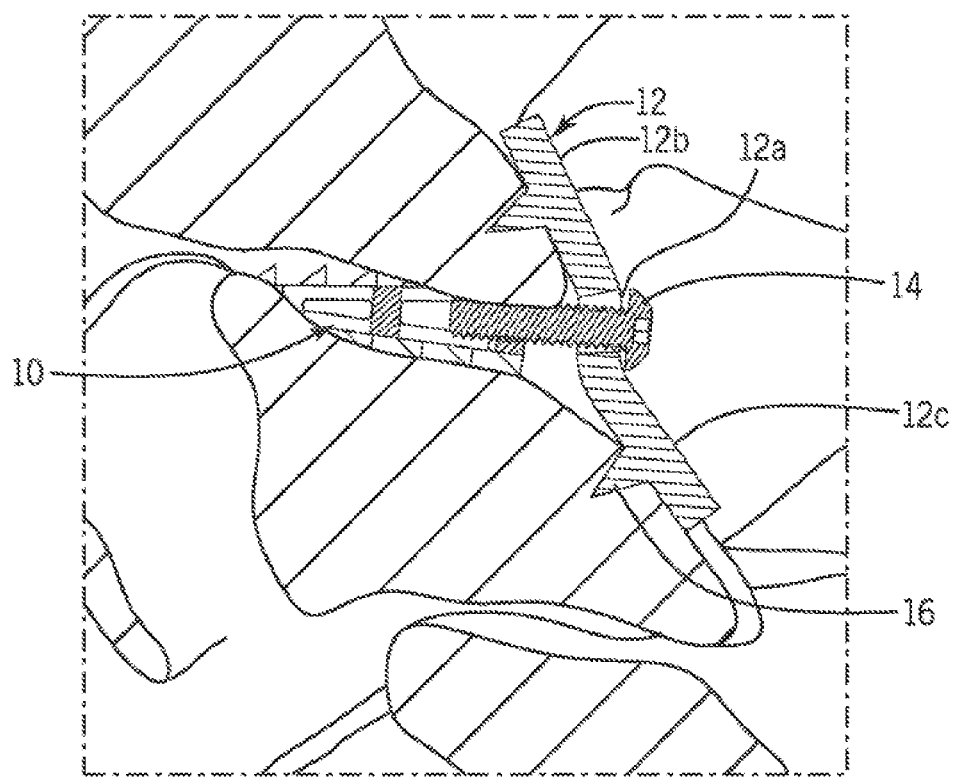

Referring now to FIGS. 3A-3D, in one embodiment, a lateral mass fixation system may include a facet implant 10, a lateral mass fixation member, such as a plate 12, and one or more screws 14 for attaching the plate 12 to the facet implant 10. The plate 12 (or "bar") may extend over the rostral and caudal lateral mass and may be attached to the back of the facet implant 10 with the screw 14, which pulls the plate 12 up snugly against the lateral mass bone and provides additional fixation. As discussed in further detail below, the plate 12 may have a middle portion 12a and a two extensions 12b, 12c extending from the middle portion 12a. The middle portion 12a includes an aperture 13 configured to receive the screw 14 for attaching the plate 12 to the facet implant 10. The plate 12 may have a fixed shape or be adjustable by, for example a hinge between the middle portion 12a and the extensions 12b, 12c. In some embodiments, the extensions 12b, 12c may be flexible to allow the plate 12 to contour to the shape of the lateral mass bone. The facet implant 10 may include one or more threaded holes 10a formed through a distal end for receiving the one or more screws 14. In various embodiments, the screws may be tightened to a desired tension such that the plate 12 is securely attached to the facet implant 10 and the lateral mass bone. Referring to FIG. 3D, the plate 12 may include one or more surface features or spikes 16 (or alternatively screws or other attachment members) at the rostral and caudal end of the plate 12, which may penetrate into the lateral masses and help secure the plate 12 to the lateral masses. The facet implant 10, plate 12 and screw 14 may be made of any suitable biocompatible material, typically a metal or combination of metals.

Figure 4:
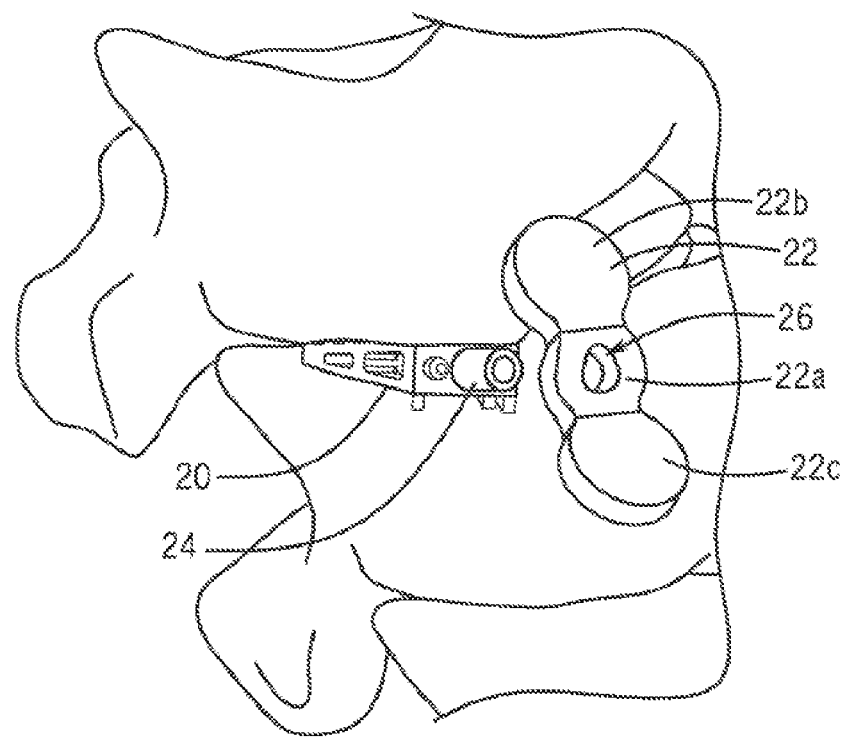
FIG. 4 is a perspective view of a portion of a cervical spine, illustrating a facet implant with a cylindrical attachment post and a lateral mass fixation member for attachment thereto, according to another embodiment.

Referring to FIG. 4, in one embodiment, a lateral mass fixation system may include a facet implant 20 with a cylindrical peg 24 (or "post") and a lateral mass fixation member, such as plate 22 with a corresponding circular opening 26 to fit around the peg 24. In various embodiments, the peg 24 may be located at a proximal end of the facet implant 20. The cylindrical peg 24 may have a hole formed therethrough which may be threaded to receive a screw (e.g., screw 14) to secure the plate 22 to the facet implant 20. As illustrated in this and other embodiments, the plate 22 may include a middle portion 22a and two extensions 22b, 22c extending at angles from the middle portion. The extension angles may be configured for fitting adjacent lateral masses. In some embodiments, the extensions 22b, 22c may be adjustable, relative to the middle portion 22a, by a physician.

Figure 5A:
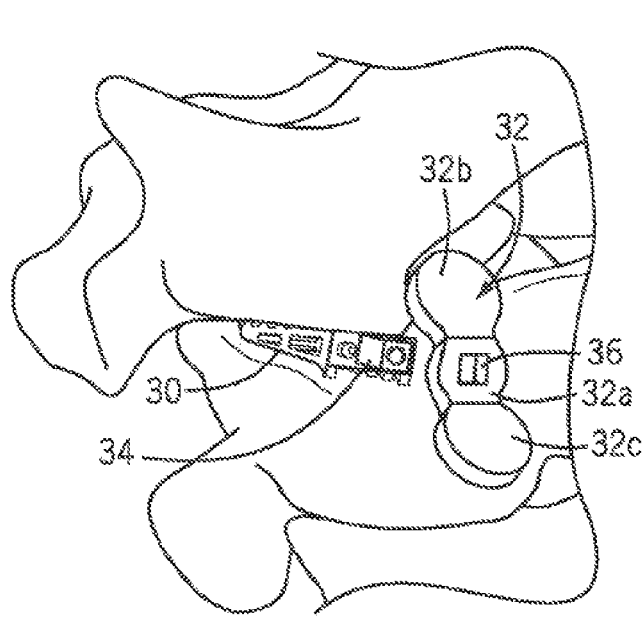
FIGS. 5A and 5B are perspective and posterior views, respectively, of a portion of a cervical spine, illustrating a facet implant with a polygonal attachment post and a lateral mass fixation member for attachment thereto, according to another embodiment.
Figure 5B:
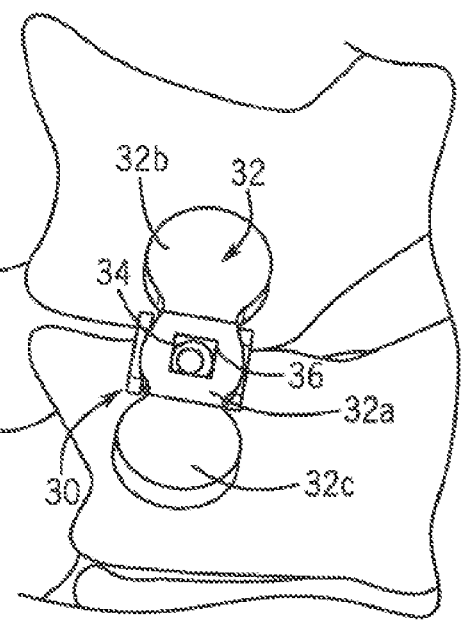

In an alternative embodiment, and referring now to FIGS. 5A and 5B, a lateral mass fixation system may include a facet implant 30 with a polygonal peg 34 (or "post," which is square in this embodiment but may have alternative shapes in other embodiments) and a lateral mass fixation member, such as plate 32 with a corresponding polygonal opening 36 to fit around or receive the peg 34. The polygonal peg 34 can orient the plate 32 to a pre-determined orientation relative to the axis of the facet implant 30, which can ensure proper contact between the plate and the lateral mass bones. As illustrated in this and other embodiments, the plate 32 may include a middle portion 32a and two extensions 32b, 32c extending at angles from the middle portion. The extension angles may be configured for fitting adjacent lateral masses. In some embodiments, the extensions 32b, 32c may be adjustable, relative to the middle portion 32a, by a physician.

Figure 6A:
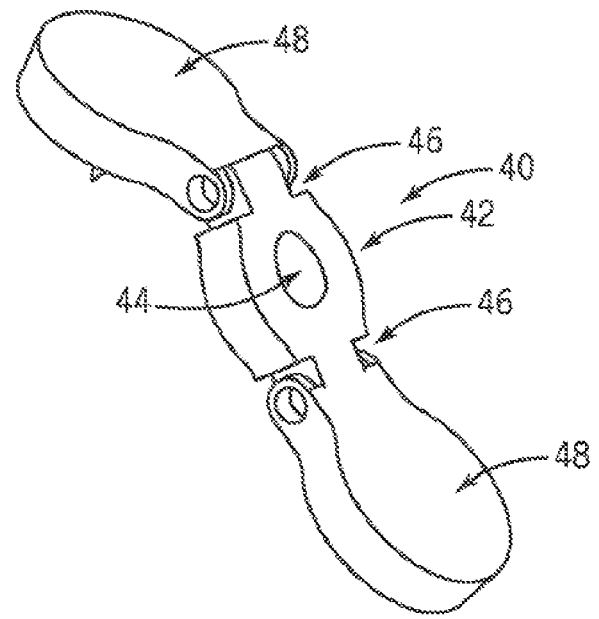
FIG. 6A is a perspective view of a jointed lateral mass fixation member, according to one embodiment.
Figure 6B:
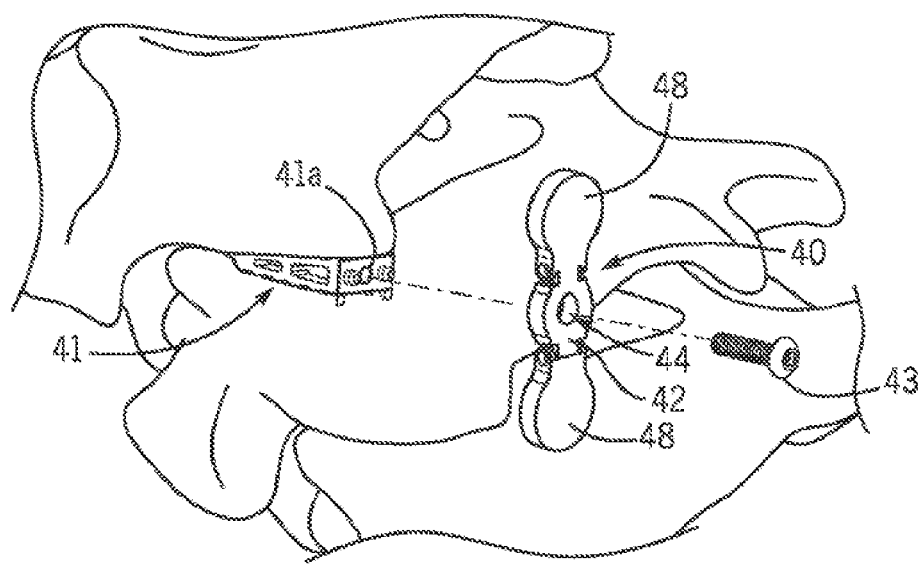
FIGS. 6B and 6C are perspective views of a portion of a cervical spine, illustrating a method for attaching the jointed lateral mass fixation member of FIG. 6A to a facet implant, according to one embodiment.
Figure 6C:
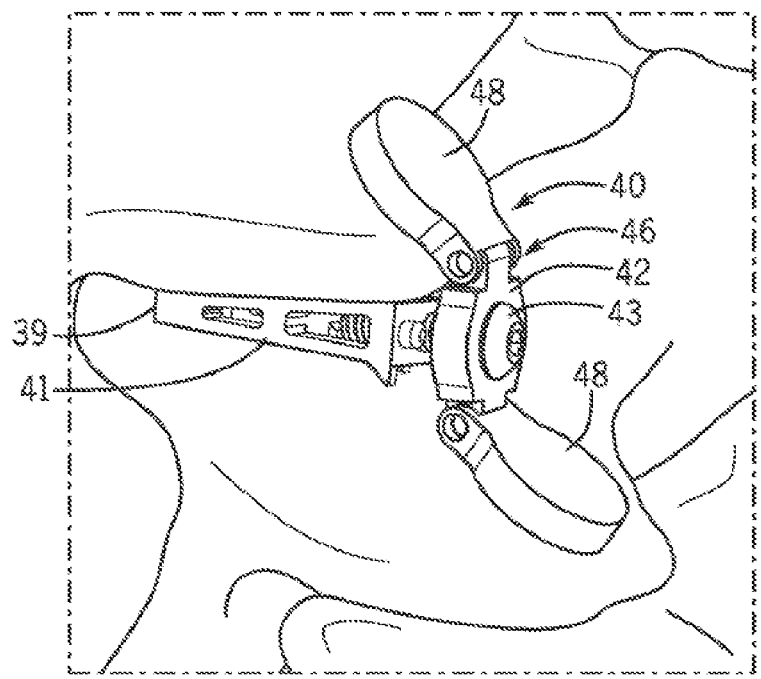

Referring now to FIGS. 6A-6C, in another embodiment, a lateral mass fixation system may include a lateral mass fixation member, such as a plate 40 that includes a middle portion 42 with a central opening 44, and two extensions 48 attached to opposite ends of the middle portion 42 via two hinges 46. The articulation of the extensions 48 about the hinges 46 will allow for adjustment of the plate 40 to fit various anatomical angles of the facet surface.

FIGS. 6B and 6C illustrate attachment of the plate 40 to a facet implant 41, using a screw 43. As can be understood from FIG. 6B, the facet implant 41 may be inserted into a facet joint 39 from a posterior access point. The plate 40 may also be inserted via a posterior access point concurrently with or subsequent to insertion of the facet implant 41. As shown in FIG. 6B, the plate 40 may have two extensions 48 which can rotate or articulate about the hinges 46. In various embodiments, the plate 40 may be inserted in a substantially linear configuration, as shown in FIG. 6B. A central opening or hole 44 through the plate 40 may be aligned with a complementary hole 41a in the facet implant 41 to receive the screw 43, which affixes the plate 40 to the facet implant 41. The extensions 48 may be rotated about the hinges 46 relative to the middle portion 42 to secure the plate 40 to the lateral masses. In various embodiments, the extensions 48 may be pre-rotated prior to insertion or may be adjusted after insertion.

Referring now to FIGS. 7A-7D, in another embodiment, a lateral mass fixation system may include a combined facet implant/lateral mass fixation device 50. The device 50 may include a facet implant portion 52 and a lateral mass fixation member or portion 54, which are connected together before implantation in the patient. The facet implant portion 52 may include a number of teeth 53 for securing the facet implant portion 52 in the facet joint. In this embodiment, the lateral mass fixation portion 54 includes two flexible, semi-rigid, or rigid members (or "tabs") 55 protruding or extending from a proximal end of the facet implant portion 52. The lateral mass fixation portion may include one or more holes 57 formed through the members 55 for receiving a securing device, such as a screw, for fixing the lateral mass fixation portions 52 to the lateral masses.

Figure 7A:
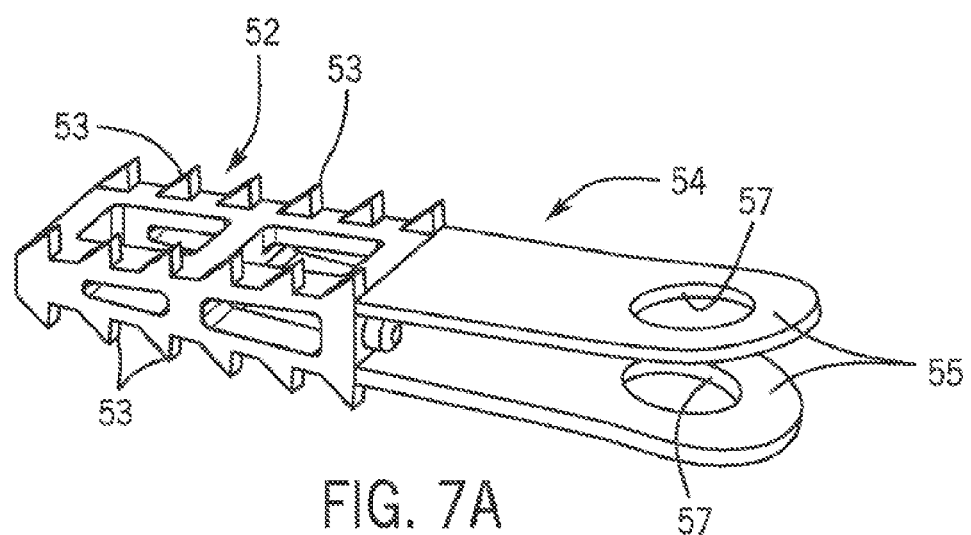
FIG. 7A is a perspective view facet implant with pre-attached lateral mass fixation member, according to one embodiment.
Figure 7B:
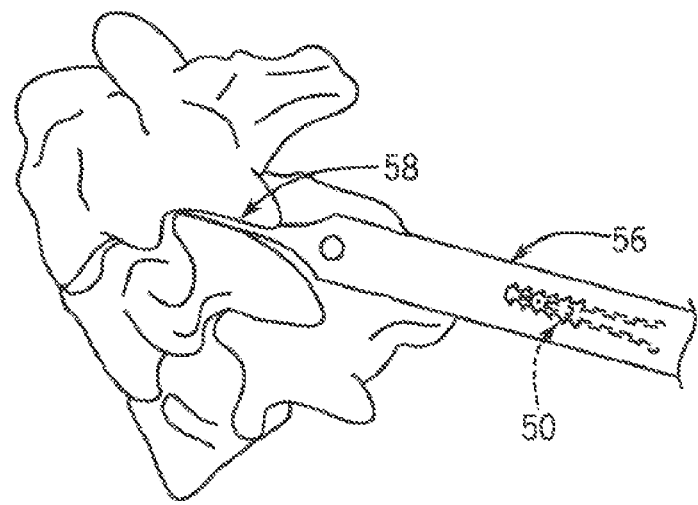
FIGS. 7B-7D are lateral (7B) and perspective (7C-7D) views of a portion of a cervical spine, illustrating a method for implanting and attaching the facet implant with pre-attached lateral mass fixation members of FIG. 7A, according to one embodiment.
Figures 7C, 7D:
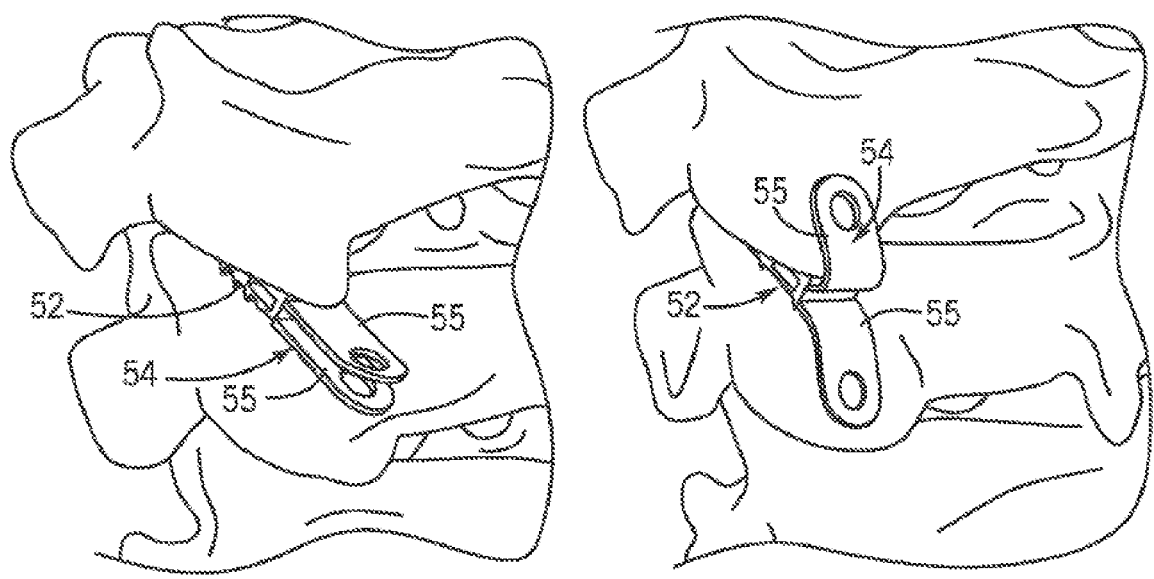

As illustrated in FIG. 7B, in one embodiment, the fixation device 50 may be advanced into the patient and into a facet joint 58 through an introducer device 56 (or "guide tube"). Referring to FIGS. 7C and 7D, once the facet implant portion 52 is implanted in the facet joint 58, the tabs 55 of lateral mass fixation portion 54 may be bent or otherwise moved to extend over the caudal and rostral lateral masses. In various alternative embodiments, the tabs 55 may move automatically by spring force, upon release from the introducer device 56, or may be bent manually or by mechanical actuation. The attachment of the lateral mass fixation portion 54 to the facet implant portion 52 allows the tabs 55 to be deployed in the desired location over the lateral masses.

Figure 8A:
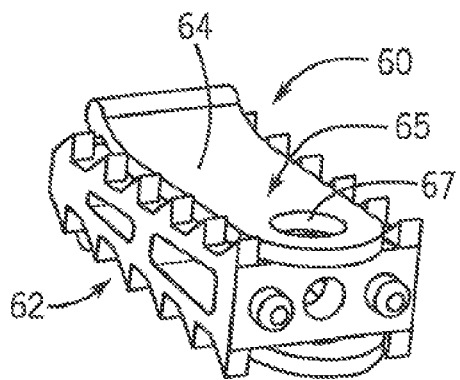
FIG. 8A is a perspective view facet implant with pre-attached lateral mass fixation members that are partially contained within the facet implant, according to one embodiment.
Figure 8B:
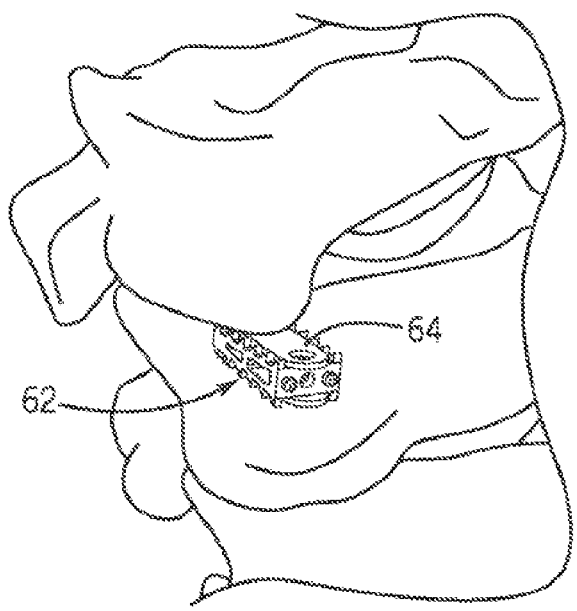
FIGS. 8B-8G are various views, some including a portion of a cervical spine, illustrating a method for implanting and attaching the facet implant with pre-attached lateral mass fixation members of FIG. 8A, according to one embodiment.
Figure 8C:
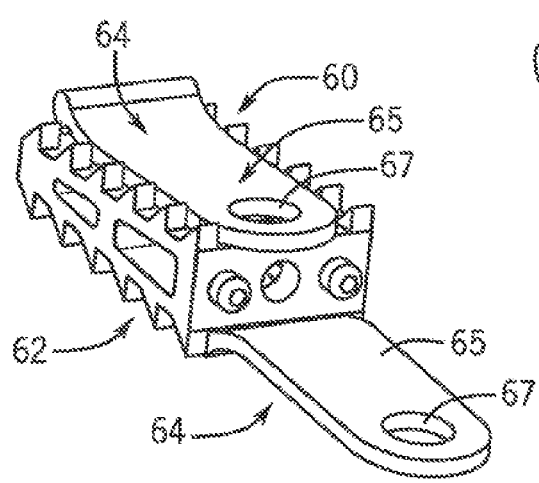
Figure 8D:
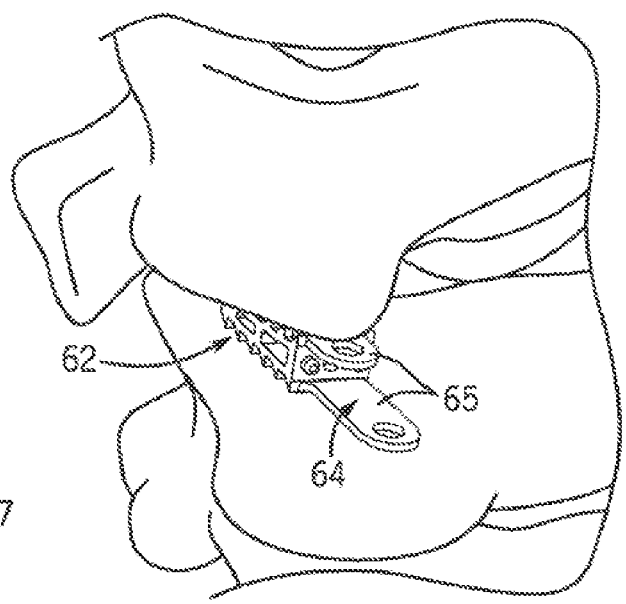

With reference now to FIGS. 8A-8G, in another alternative embodiment, a lateral mass fixation device 60 may include a facet implant portion 62 and a lateral mass fixation member or portion 64, which are connected together before implantation in the patient. In this embodiment, the lateral mass fixation portion 64 includes two flexible, semi-rigid, or rigid members (or "tabs") 65 that are at least partially housed within the outer diameter of the facet implant portion 52 during delivery into the patient. The tabs 65 may include apertures or holes 67 defined therein for receiving a screw or other securing device. FIGS. 8A and 8B illustrate the fixation device 60 in its delivery configuration, with the tabs 65 housed within the facet implant portion 62. FIGS. 8C and 8D illustrate the fixation device 60 with one of the tabs 65 extending outward (proximally) from the facet implant portion 62. This extension motion may be achieved by sliding the tab 65 along a slot in the facet implant portion 62, for example.

Figures 8E, 8F:
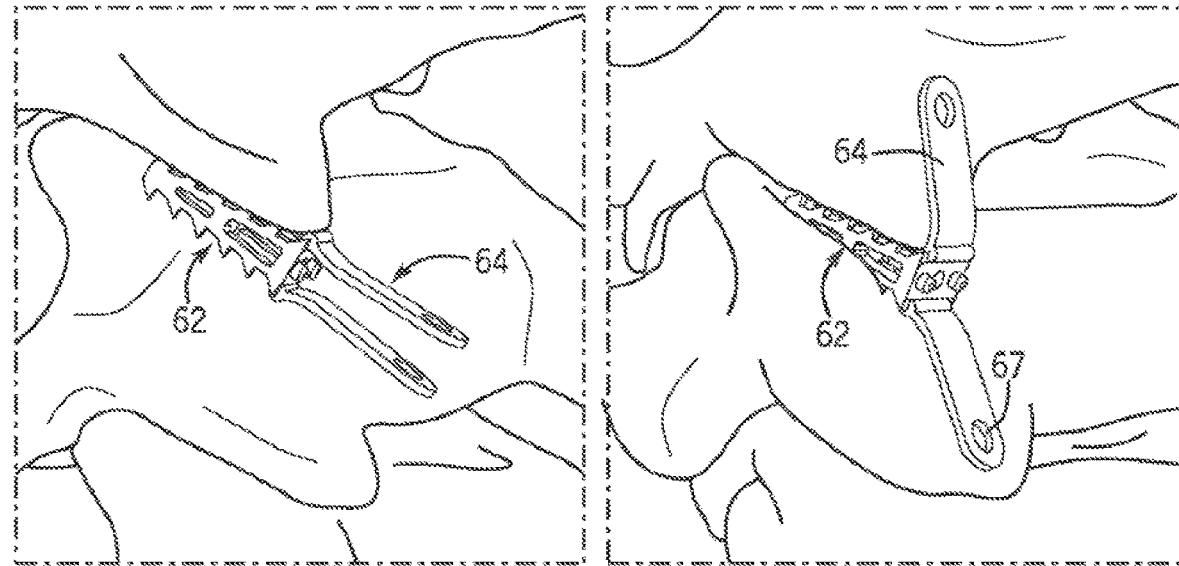
Figure 8G:
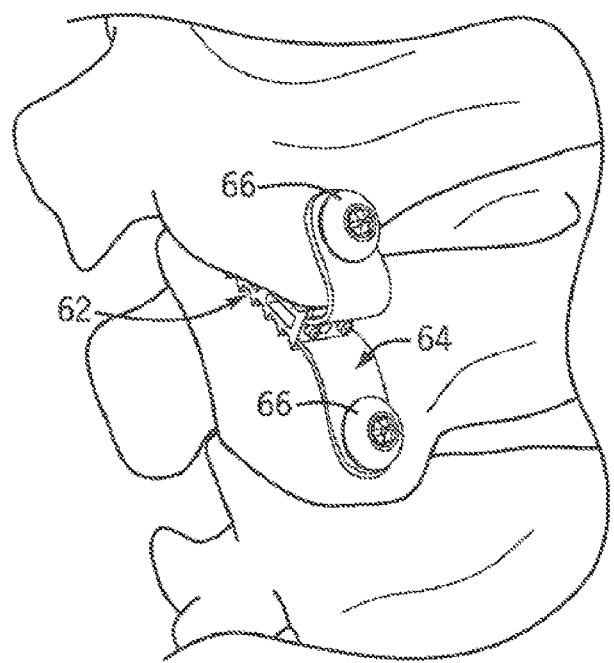

FIG. 8E shows the fixation device 60 with both tabs 65 of the lateral mass fixation portion 64 extended. FIG. 8F shows the tabs 65 in a bent configuration to contact the caudal and rostral lateral masses. FIG. 8G shows the tabs 65 attached to the lateral masses via screws 66 received in the apertures 67.

Figures 9A, 9B:
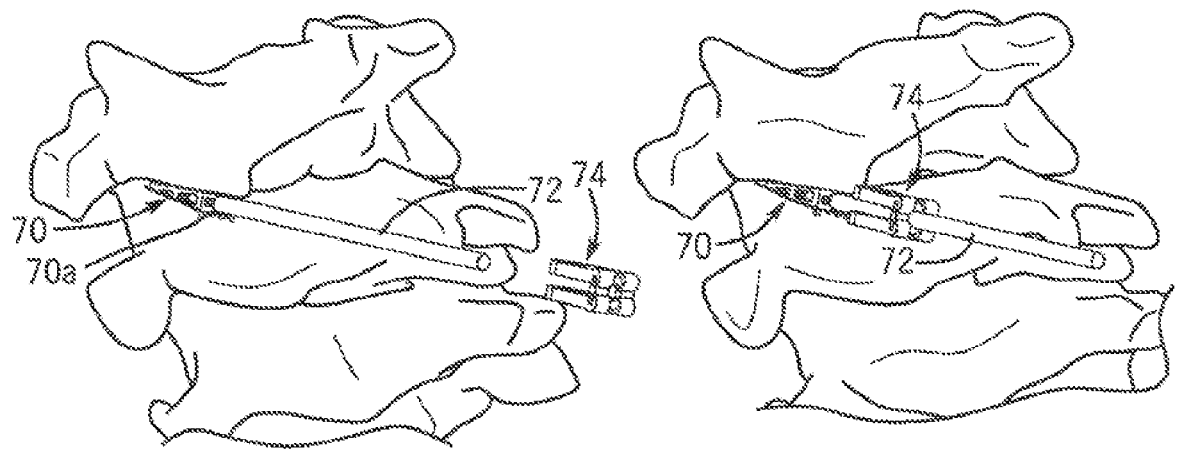
FIGS. 9A-9D are perspective views of a portion of a cervical spine, illustrating a method for advancing a folded lateral mass fixation member over a guide rod for attachment to a facet implant, according to one embodiment.
Figure 9C:
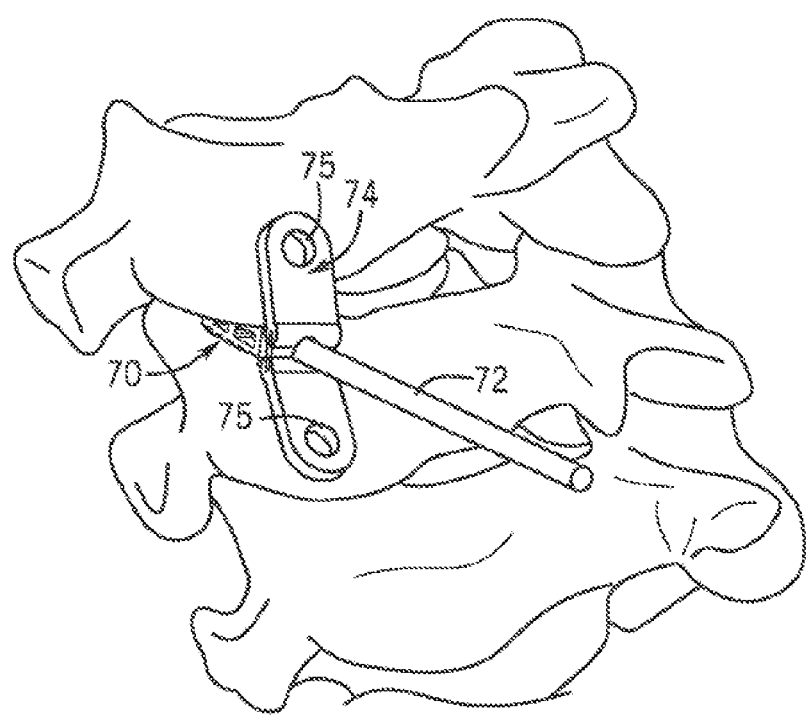
Figure 9D:
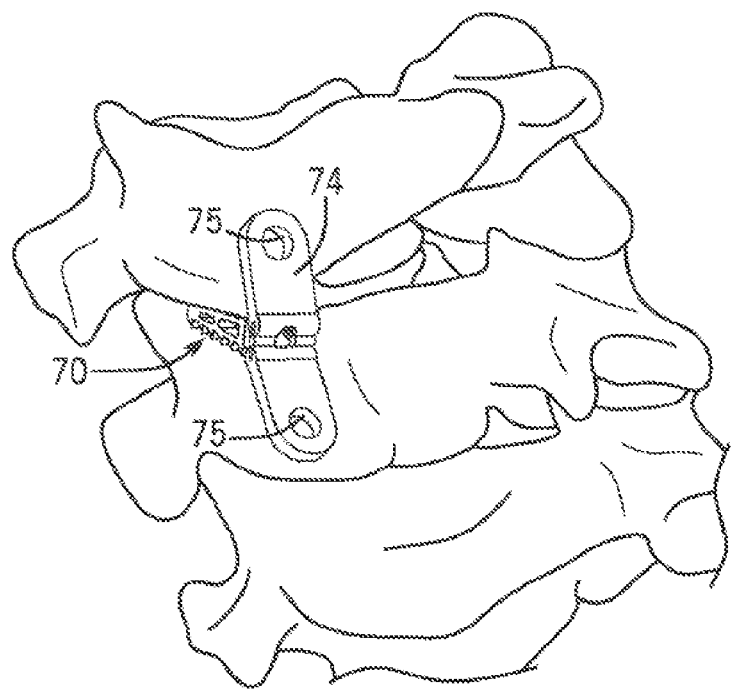
Figures 10A, 10B:
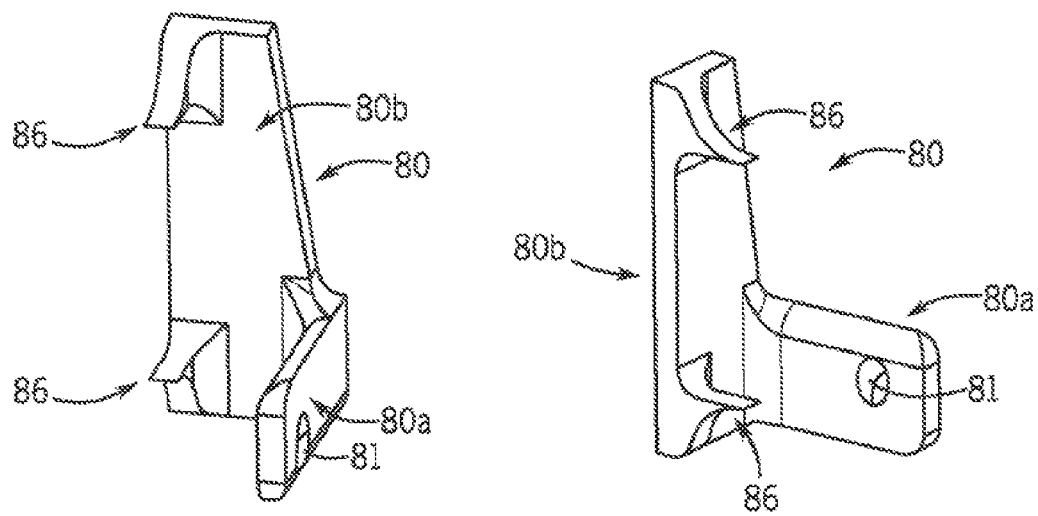
FIGS. 10A and 10B are perspective views of a lateral mass fixation member, according to one embodiment.
Figure 10C:
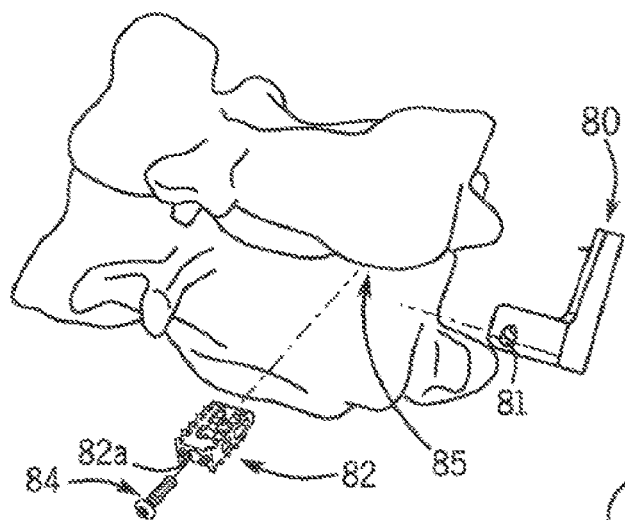
FIGS. 10C-10F are perspective views of a portion of a cervical spine, illustrating a method for attaching the lateral mass fixation member of FIGS. 10A and 10B to a facet implant, according to one embodiment.
Figure 10D:
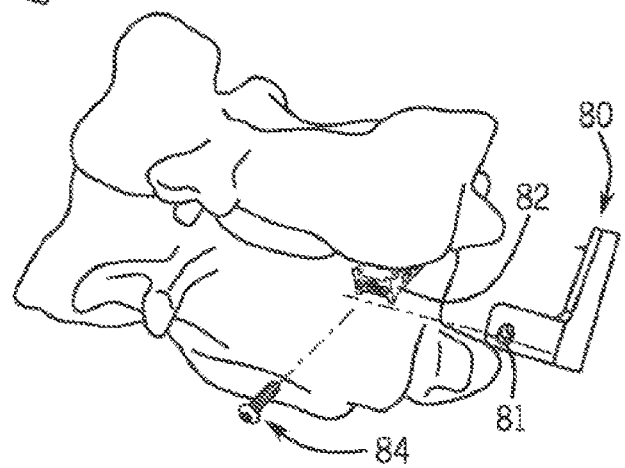
Figure 10E:
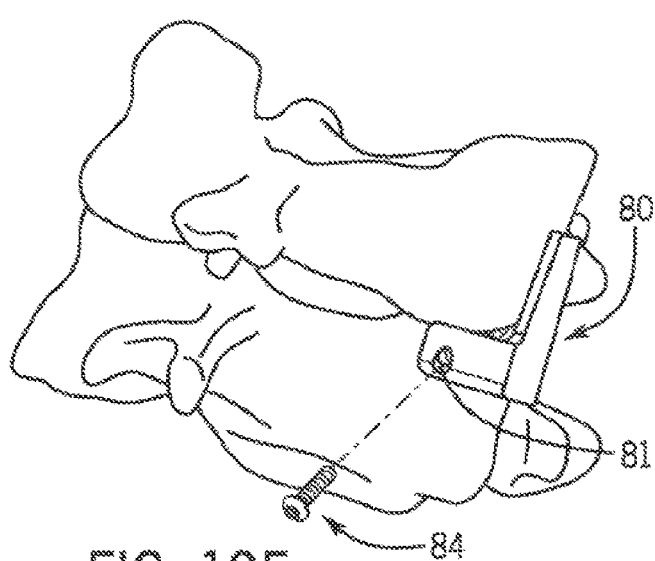
Figure 10F:
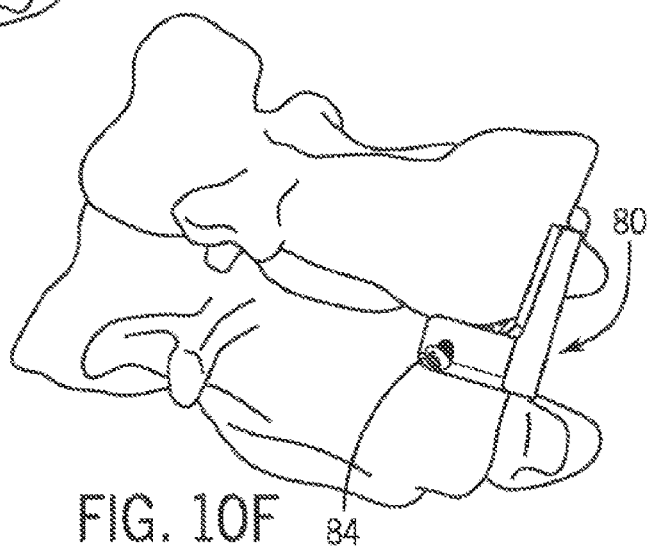

In yet another embodiment, and referring now to FIGS. 9A-9D, a lateral mass fixation system may include a facet implant 70, a guide rod 72 removably attached to the proximal end 70a of the facet implant 70, and a lateral mass fixation member 74 that is slidable over the guide rod 72. As illustrated in the figures, the lateral mass fixation member 74 may be advanced over the guide rod 72 in a collapsed configuration (FIGS. 9A and 9B) and then expanded to contact the lateral masses (FIG. 9C). The guide rod 72 may then be removed (FIG. 9D), leaving the facet implant 70 and lateral mass fixation member 74 in place. Screws (not shown) may be inserted through the holes 75 in the lateral mass fixation member 74 to attach the lateral mass fixation member 74 to the lateral masses.

Referring now to FIGS. 10A-10F, in another embodiment, a lateral mass fixation member or plate 80 may include one or more surface features, such as spikes 86 for enhancing attachment to bone. The lateral mass fixation plate 80 may include two portions 80a, 80b, which may be arranged substantially perpendicular to one another. The first portion 80a may have a hole 81 formed therethrough to receive a screw or other attachment device. The second portion 80b may have the spikes 86 extending therefrom. The spikes 86 may extend substantially parallel to the first portion 80a. FIGS. 10C-10F illustrate a method for implanting a facet implant 82 and attaching the lateral mass fixation plate 80 to the facet implant 82 via a screw 84. The facet implant 82 may be inserted into the facet joint 85. The plate 80 may be inserted such that the hole 81 formed through the first portion 80a aligns with a hole 82a in the facet implant 82. The second portion 80b of the plate 80 may abut the lateral mass and secure the plate 80 and facet implant 82 in place when the screw 84 is inserted through the plate 80 into the facet implant 82. In an alternative embodiment, the lateral mass fixation plate 80 may have any of a number of different shapes, sizes, spikes or other surface features, and/or the like. Furthermore, in various embodiments, the lateral mass fixation plate 80 may be flexible, semi-rigid, or segmented.

Figure 11A:
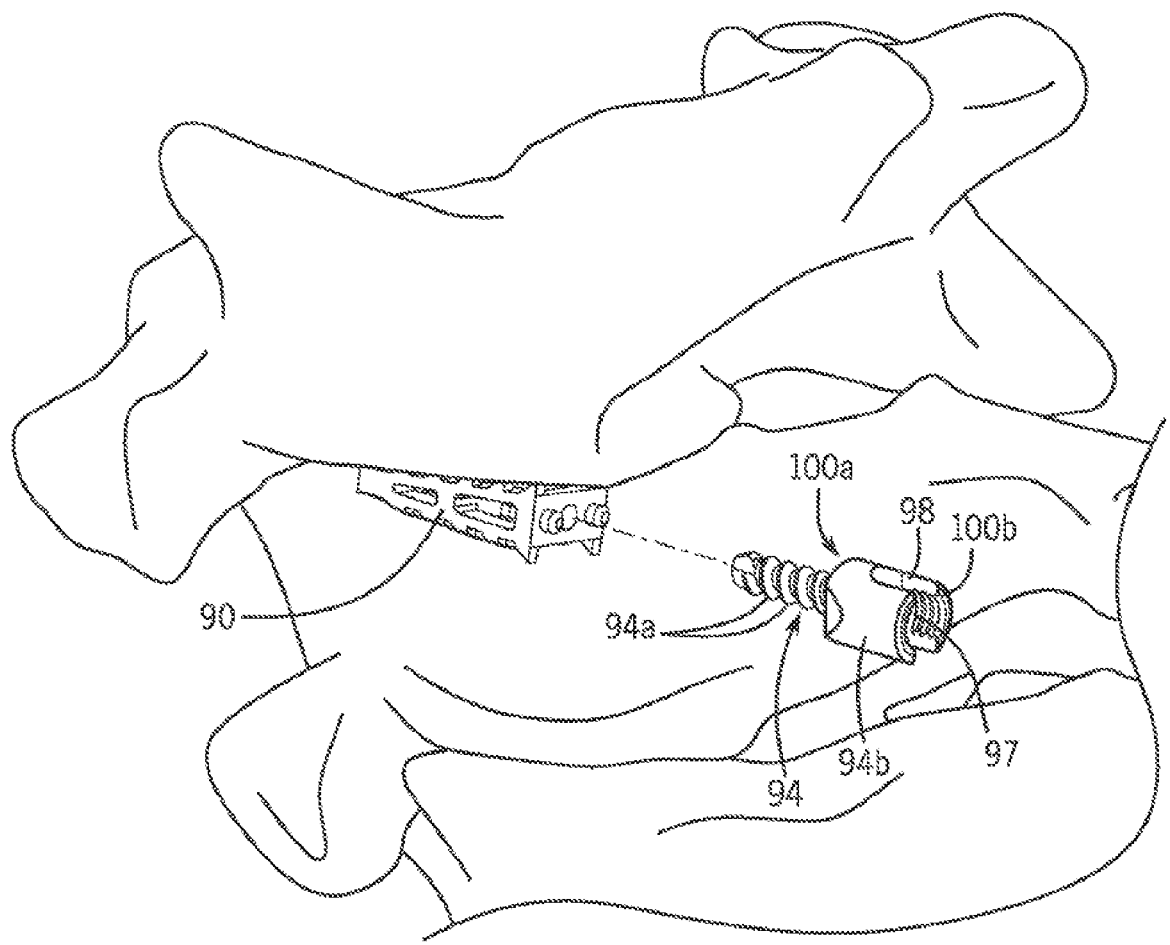
FIGS. 11A-11H are various views of a cervical spine illustrating a system including a facet implant and a lateral mass fixation member and a method of attaching the lateral mass fixation member to the fact implant.
Figure 11B:
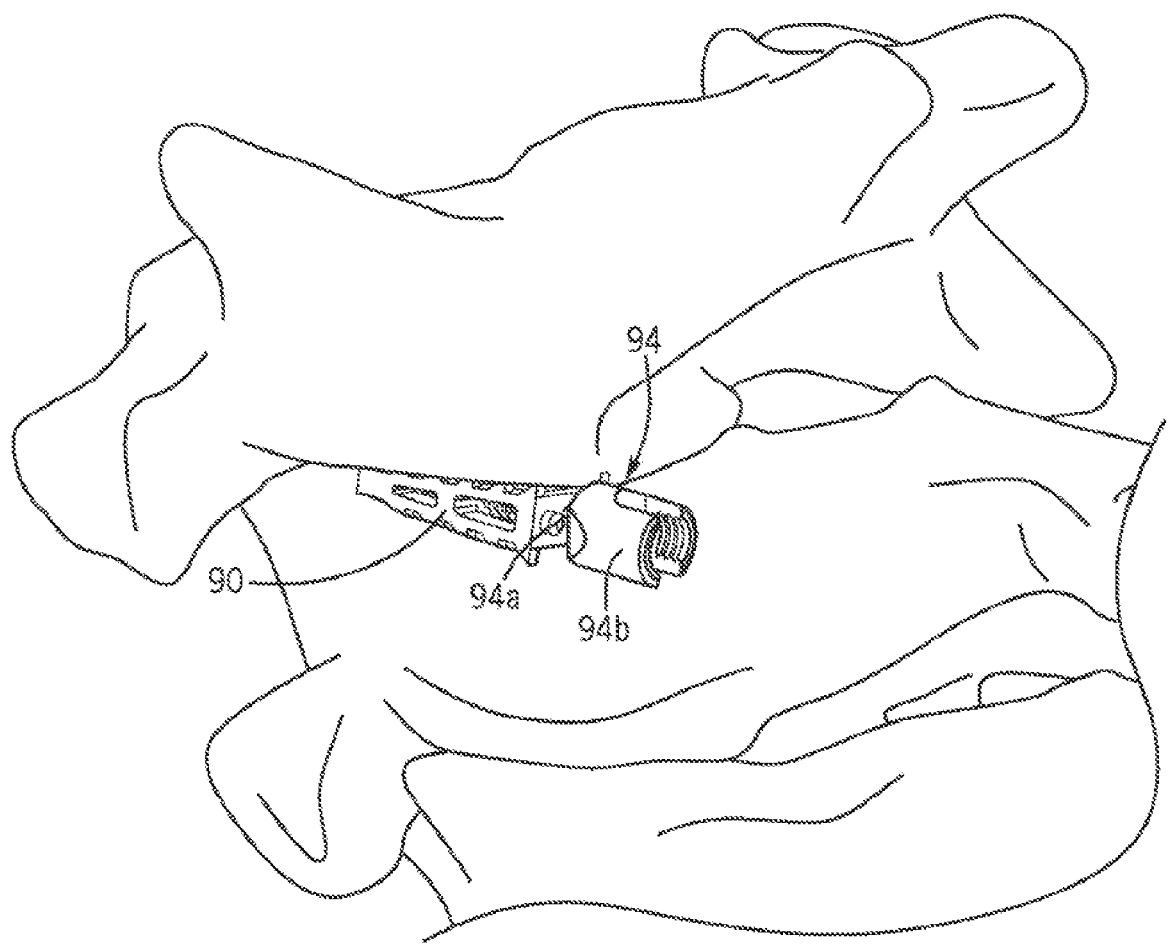
Figure 11C:
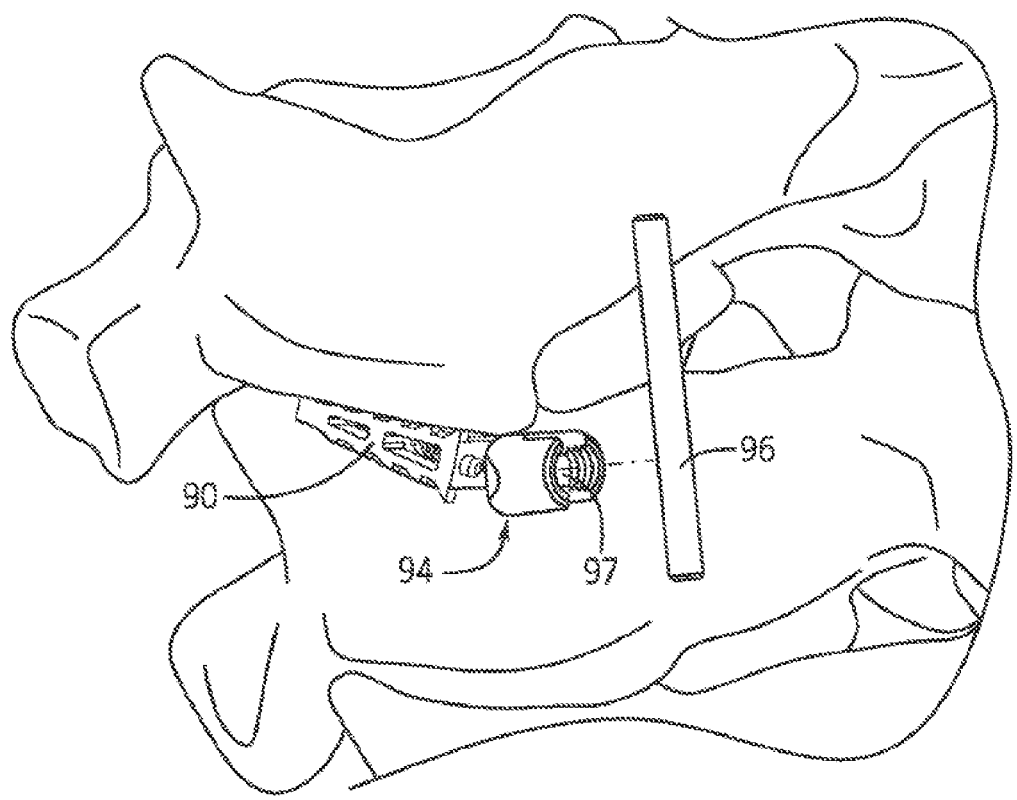
Figure 11D:
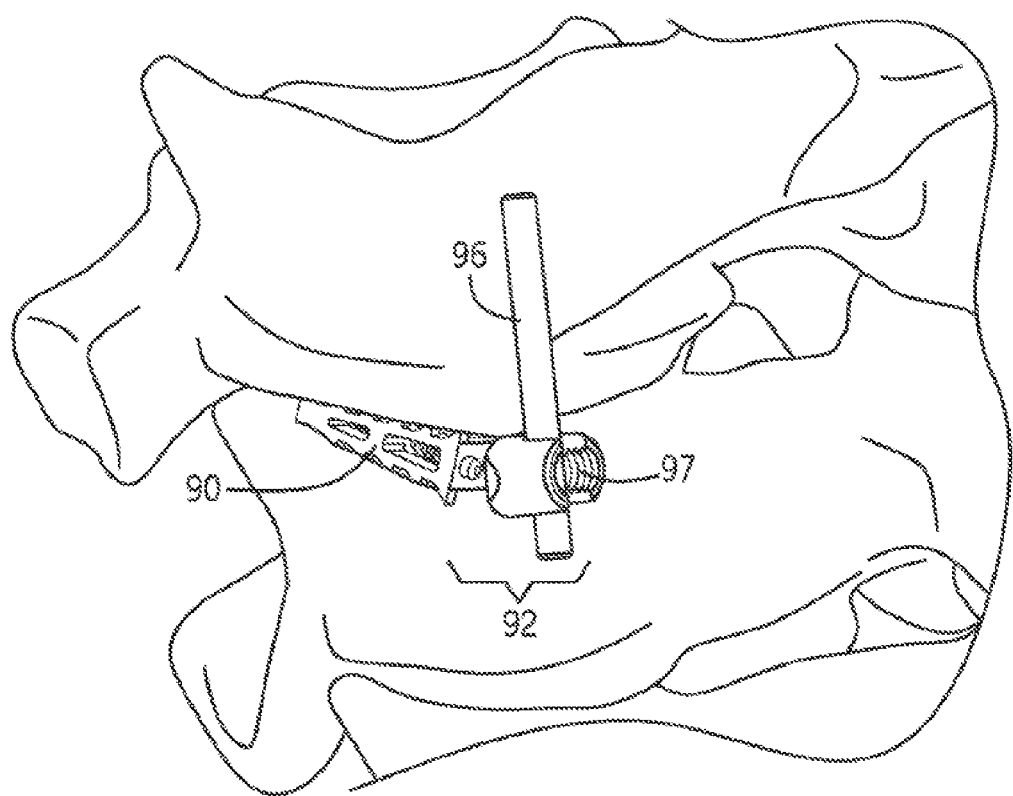
Figure 11E:
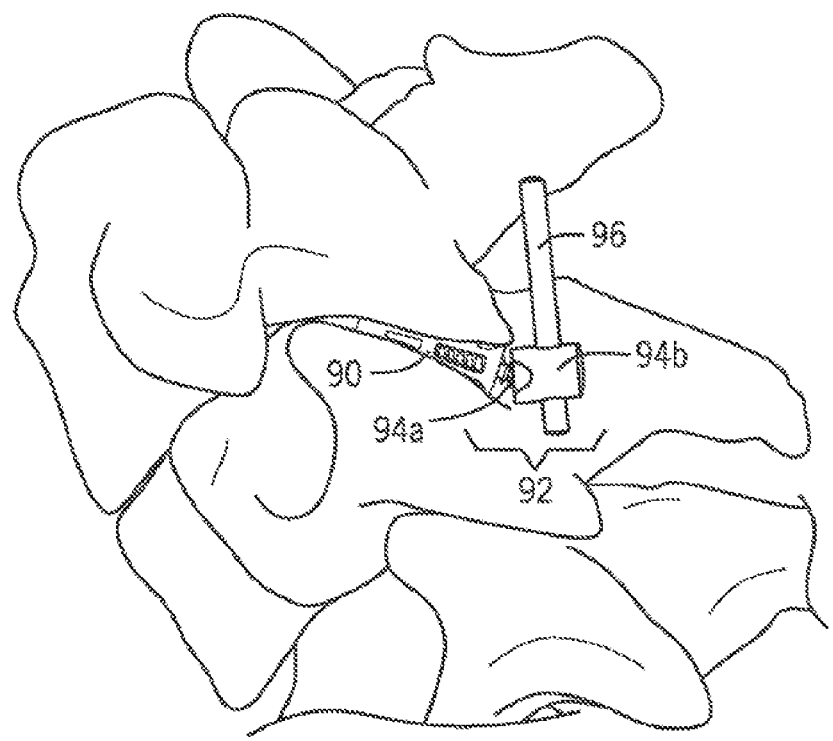
Figure 11F:
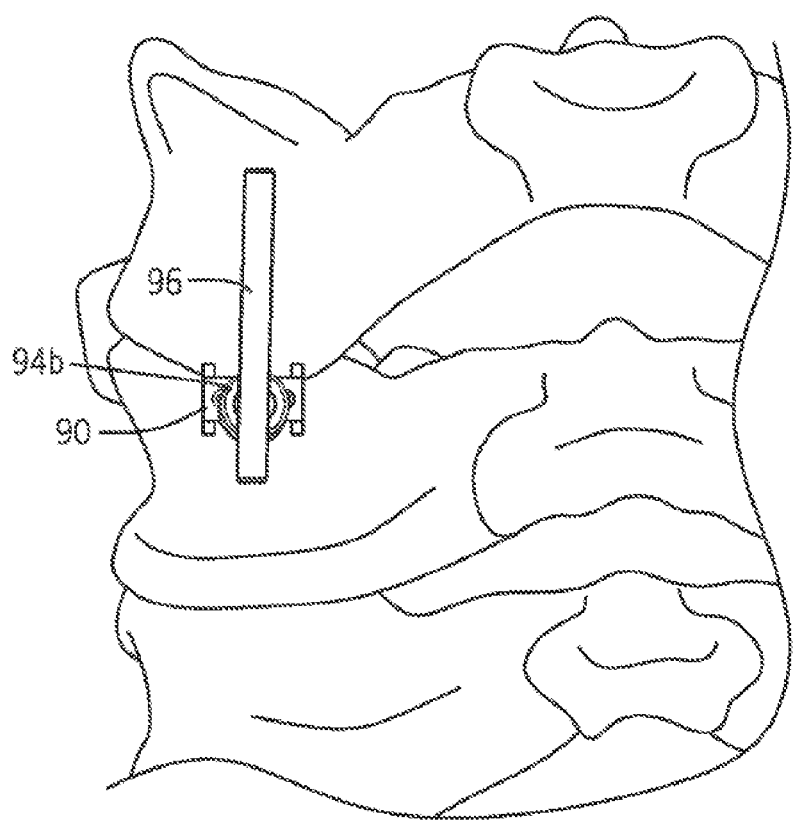
Figure 11G:
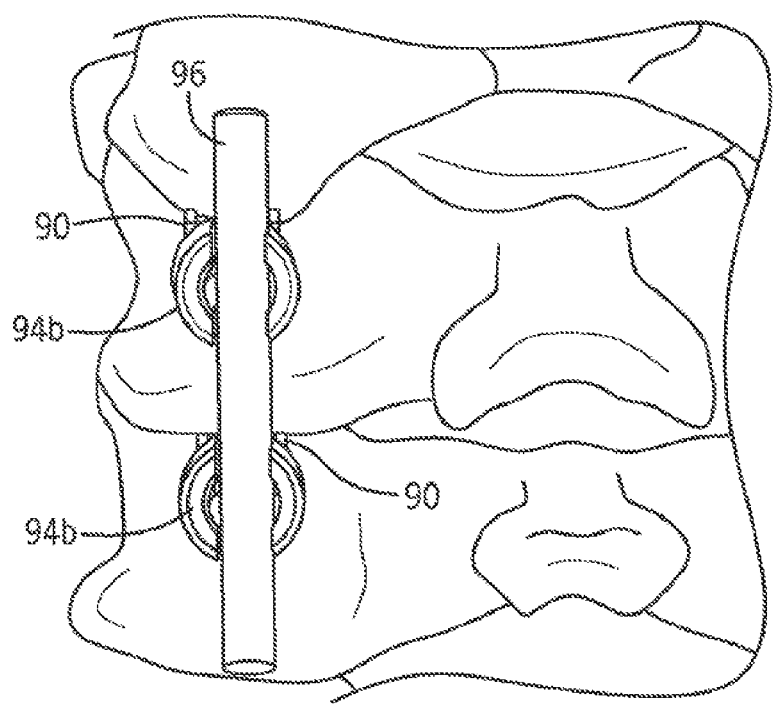
Figure 11H:
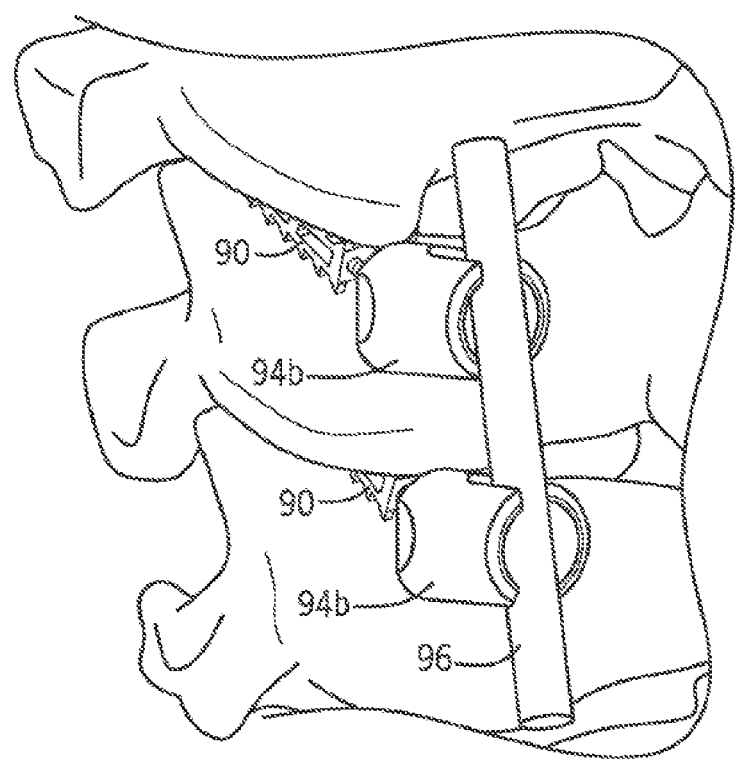

Referring now to FIGS. 11A-11C, in one embodiment, a lateral mass fixation system may include a facet implant 90 and a lateral mass fixation member 92 including an anchor 94 and a rod 96. As shown in FIG. 11A, and others, the anchor 94 includes an attachment device 94a, such as a screw, and a rod receiving member 94b. The rod receiving member 94b has a generally cylindrical body having proximal and distal ends 100a, 100b, with threads 97 and an open ended slot 98 sized to receive the rod 96 at the distal end 100b of the body. The rod 96 may extend across the facet joint and may be attached to the facet implant 90 via the anchor 94, which pulls the rod 96 up snugly against the lateral mass bone and provides additional fixation. FIG. 11B illustrates attachment of the anchor 94, via the attachment device 94a, to the implant 90, which has already been inserted in the facet joint. As can be understood from FIGS. 11C-11F, the rod 96 is introduced into the slot 98 of the rod receiving member 94b and secured therein. As indicated in FIGS. 11E-11F, which are side and posterior views of the facet implant 90 and lateral mass fixation member 92, the lateral mass fixation member 92 may be adjusted via rotation of the anchor 94 to secure or fix the rod 96 against the lateral masses. In some embodiments, as illustrated in FIGS. 11G-11H, which are posterior and posterior isometric views of the system, a plurality of facet implants 90 hold the rod 96 to stabilize the spine.

All relative and directional references (including: upper, lower, upward, downward, left, right, leftward, rightward, top, bottom, side, above, below, front, middle, back, vertical, horizontal, and so forth) are given by way of example to aid the reader's understanding of the particular embodiments described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

Although the invention has been disclosed in the context of certain embodiments and examples, the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. A spinal implant system, comprising:
   a facet implant member for positioning in a facet joint, the implant having a proximal end and distal end; and
   a lateral mass fixation member attached to or attachable to the facet implant member at
   the proximal end, wherein the lateral mass fixation member comprises:
      an anchor comprising:
         a rod receiving member, and
         at least one attachment device for attaching the rod receiving member to
         the facet implant member; and
      a rod received in the anchor to bridge a lateral mass of adjacent vertebrae,
   wherein the facet implant member has a longitudinal axis, the facet joint has a longitudinal axis, and, in use, the longitudinal axis of the implant and the longitudinal axis of the facet joint are generally parallel or coaxial,
   wherein the at least one attachment device is received by the facet implant member along the longitudinal axis of the implant, and at least a portion of both the rod receiving member and the attachment device extend from the proximal end of the implant and are configured to extend outside of the facet joint.

2. A system as in claim 1, wherein the facet implant member and the lateral mass fixation member are two separate devices that are attachable in situ.

3. A system as in claim 1, wherein the facet implant member and the lateral mass member comprise one, attached device.

4. A system as in claim 1, further comprising a guide member for guiding at least one of the facet implant member or the lateral mass fixation member to a spine for attachment thereto.

5. The spinal implant system of claim 1, wherein the facet implant member is an intrafacet implant member.

6. The spinal implant system of claim 1, wherein the facet joint is a cervical facet joint.

7. The spinal implant system of claim 1, wherein the facet implant member includes one or more teeth for securing the facet implant member in the facet joint.

8. The system of claim 1, wherein the at least one attachment device is a screw.

9. The system of claim 1, wherein:
the facet joint is defined by two adjacent cervical vertebrae,
the implant member comprising:
- a first surface having one or more teeth extending outwardly therefrom and is configured to engage a superior articulating surface of one of the two adjacent vertebrae, and
- a second surface having one or more teeth extending outwardly therefrom and configured to engage an inferior articulating surface of the other of the two adjacent vertebrae.

10. The system of claim 1 wherein the rod receiving member further comprises a slot configured to receive the rod.

* * * * *